United States Patent
Evans et al.

(10) Patent No.: US 6,773,160 B2
(45) Date of Patent: Aug. 10, 2004

(54) PHOSPHOR IMAGING PLATE AND CASSETTE HANDLING SYSTEM

(75) Inventors: Wayne Evans, Campbell, CA (US); H. Keith Nishihara, Los Altos, CA (US); Brian P. Wilfley, Los Altos, CA (US); Douglas A. Reim, San Jose, CA (US); William F. Witt, Palo Alto, CA (US); Sung Kim, Palo Alto, CA (US); Ron Smith, Foster City, CA (US); Perry Anderson, Berkeley, CA (US); Heather Klaubert, Redwood City, GA (US); Gary Cantu, Foster City, CA (US); James Olef Jensen, Mountain View, CA (US); Eric J. Shrader, Belmont, CA (US)

(73) Assignee: Alara, Inc., Hayward, CA (US)

( * ) Notice: Subject to any disclaimer, the term of this patent is extended or adjusted under 35 U.S.C. 154(b) by 0 days.

(21) Appl. No.: 09/847,857

(22) Filed: May 1, 2001

(65) Prior Publication Data

US 2003/0123613 A1 Jul. 3, 2003

Related U.S. Application Data

(60) Provisional application No. 60/201,324, filed on May 2, 2000.

(51) Int. Cl.[7] .............................................. G03B 41/00
(52) U.S. Cl. ..................... 378/173; 378/174; 250/588
(58) Field of Search ................................. 250/588, 580, 250/581, 584, 589, 590; 378/174, 173, 172

(56) References Cited

U.S. PATENT DOCUMENTS

| | | | |
|---|---|---|---|
| 4,476,873 A | 10/1984 | Sorenson et al. ........... 128/660 |
| 4,659,929 A | * 4/1987 | Fujiwara et al. ............. 250/589 |
| 4,861,995 A | * 8/1989 | Ohgoda ....................... 250/589 |
| 5,081,355 A | * 1/1992 | Miyagawa et al. .......... 250/582 |
| 5,095,209 A | 3/1992 | Tamura |
| 5,623,146 A | 4/1997 | Jones et al. .................. 250/334 |
| 5,635,728 A | 6/1997 | Cantu et al. ................. 250/584 |
| 6,121,629 A | 9/2000 | Koishikawa et al. |
| 6,201,628 B1 | 3/2001 | Basiji et al. ................. 359/212 |
| 6,355,938 B1 | 3/2002 | Cantu et al. ................. 250/584 |
| 2003/0123613 A1 | 7/2003 | Evans et al. ................. 378/146 |

FOREIGN PATENT DOCUMENTS

| JP | 36226632 A | * 9/1988 | |
|---|---|---|---|
| WO | WO 00/19477 | 9/1999 | ........... G01N/23/04 |

* cited by examiner

Primary Examiner—David V. Bruce
Assistant Examiner—Hoon Song
(74) Attorney, Agent, or Firm—Heller Ehrman White & McAuliffe LLP

(57) ABSTRACT

A combined imaging plate scanning and erasing system, comprising: (a) a housing; (b) an imaging plate cassette infeed assembly positioned within the housing, the maging plate cassette infeed assembly comprising: (i) a mechanism to pull an imaging plate cassette into the housing; (ii) a mechanism to open the imaging plate cassette; and (iii) a mechanism to remove an imaging plate from the cassette; (c) a scanner positioned within the housing; (d) a curved path erasing assembly positioned between the imaging plate infeed assembly and the scanner; and (e) an imaging plate transportation assembly to move the imaging plate back and forth in a path extending from the imaging plate cassette, past the erasing assembly and through a scan area adjacent to the scanner.

104 Claims, 23 Drawing Sheets

PHOSPHOR IMAGING PLATE AND CASSETTE HANDLING SYSTEM

CROSS-REFERENCES TO RELATED APPLICATIONS

This application is a continuation of, and claims the benefit of priority from U.S. Application No. 60/201,324, filed May 2, 2000, the full disclosure of which is incorporated herein by reference.

TECHNICAL FIELD

The present invention relates both to imaging plate scanning systems and to imaging plate erasing systems. In general, the present invention relates to all forms of medical imaging plates, however, a particular preferred application of the present invention is related to storage phosphor imaging plates.

BACKGROUND OF THE INVENTION

Imaging plates, such as storage phosphor imaging plates, have become standard in the field of Computed Radiography (CR) as the medium onto which an image of a portion of the patient's body can be stored. The image on such a phosphor imaging plate is extracted by scanning the imaging plate with a scanner. Typically, a phosphor imaging plate is scanned by passing a scanning laser beam over the surface of the imaging plate while recording light emitted from the imaging plate in response to the laser beam. By recording the emission corresponding to each of the pixels of the imaging plate with a detector such as a photomultiplier, the image stored therein can be re-created (such that it can be displayed on a computer terminal).

The act of scanning an imaging plate by passing a scanning laser beam thereacross is inherently destructive (i.e.: it releases the energy stored in the phosphor screen). As such, a particular image stored on an imaging plate can only be scanned (i.e. read) once. Although such scanning of the imaging plate releases the image, thereby erasing the image, such erasure is not complete and the imaging plate may still contain ghost images, lines or other image artifacts caused or not yet fully erased by the scanning procedure itself. Accordingly, it is necessary to completely and evenly erase an imaging plate before it can be re-used to store another image thereon.

To preserve a high image quality, phosphor imaging plates are typically housed within imaging plate cassettes to protect them from light, dust, fingerprints, and other image quality reducing artifacts. Such cassettes offer protection for the imaging plates, thus ensuring a long life such that the imaging plate can be reused again and again.

To reuse an imaging plate, it must first be scanned, and then erased. Both scanning and erasing release images on the imaging plate by exposing the imaging plate to roughly the same visible wavelength of light. It is, therefore, important to ensure that the imaging plate is not inadvertently exposed to such erasing wavelengths of light prior to scanning. Accordingly, scanning and erasing of the imaging plates are typically carried out in different machines, or at widely spaced apart locations within the same machine. When separate scanning and erasing machines are used, the imaging plate is typically hand transported therebetween while stored in the imaging plate cassette. Specifically, the phosphor imaging plates are first scanned in a scanner, and then are hand carried and placed into a separate erasing machine which passes the plate under a suitable wavelength of light such that all images stored therein are released.

Therefore, it is desirable to provide a combined imaging plate scanning and erasing system such that it is not necessary to remove an imaging plate from a cassette, scan it with a scanner, remove it from the scanner, place it back into the cassette, hand carry the cassette to an erasing machine, insert the imaging plate into the erasing machine, erase the imaging plate and then return the imaging plate to the cassette for future use.

Another problem common to both scanning and erasing machines is the manner in which the imaging plates are removed from the cassette. Sometimes, this is simply done by hand (with the imaging plates then placed by hand into the scanner or eraser). In addition, a variety of bulky systems using vacuum, gravity, or friction extraction motorized devices have been used to remove an imaging plate from a cassette. One problem with such systems are that they often tend to handle the imaging plate rather roughly. This is especially true of gravity systems in which the cassette is opened such that the imaging plate simply falls into a machine.

Therefore, it is desirable to provide a system which gently and automatically removes an imaging plate from a cassette prior to scanning and gently and automatically returns the imaging plate to the cassette after the imaging plate has been erased.

Yet another problem common to existing imaging plate scanners and to existing imaging plate erasing machines is that they tend to be very large. This is especially true in the case of large combined scanning and erasing systems due to the fact that large numbers of imaging plate and imaging plate cassette designs are already in circulation. Accordingly, manufacturers tend to design scanning and erasing machinery which is adapted to deal with these pre-existing plate and cassette designs, rather than simultaneously design imaging plates, cassettes, scanners and erasing systems which would together operate to provide more spatially integrated and efficient systems. Existing cassette designs, in particular, are often poorly suited to automation, necessitating large, bulky scanning and erasing systems which are not designed to handle these imaging plates (and their associated cassettes) within small spaces.

Moreover, in many of these large existing systems, it is typically necessary to position the scanning mechanism some distance from the erasing mechanism simply to prevent light from the erasing mechanism from entering the scanning mechanism. Being so large, these existing systems must unfortunately move the imaging plate through a considerable distance therein. Such long pathways of travel (which require many separate devices to move and position the imaging plate at various locations therein) have many drawbacks. For example, complex positioning systems which move imaging plates considerable distances frequently introduce positioning errors which can cause imaging problems, or simply cause the imaging plate to jam while moving through the system. Extracting a jammed imaging plate from a location deep within a scanner or erasing system can be frustrating and time consuming.

Therefore, it is especially desirable to provide a compact combined imaging plate scanning and erasing system which is much smaller than existing systems, moving its imaging plate a shorter distance Advantages of such a system would include its portability, space saving size, reduced system complexity, and increased ease and speed of operation.

SUMMARY OF THE INVENTION

The present invention provides a small, compact combination system for both scanning and then erasing an imaging plate. Although the present invention is ideally suited for use with storage phosphor imaging plates (also known as imaging "screens"), it is not so limited.

The present system comprises a compact housing into which an imaging plate cassette is first inserted. An imaging plate infeed assembly within the housing is provided to pull the imaging plate cassette into the housing, open the imaging plate cassette (when it is positioned within the housing) and then remove the imaging plate from the imaging plate cassette for scanning followed by erasing.

In a preferred aspect, the present invention provides a combined imaging plate scanning and erasing system which comprises: (a) a housing; (b) an imaging plate infeed assembly positioned within the housing, the imaging plate cassette infeed assembly comprising: (i) a mechanism to pull an imaging plate cassette into the housing; (ii) a mechanism to open the imaging plate cassette; and (iii) a mechanism to remove an imaging plate from the cassette; (c) a scanner positioned within the housing; (d) a curved path erasing assembly positioned between the imaging plate infeed assembly and the scanner; and (e) an imaging plate transportation assembly to move the imaging plate back and forth in a path extending from the imaging plate cassette, past the erasing assembly and through a scan area adjacent to the scanner.

In preferred aspects, the entire body of the imaging plate cassette is pulled fully within the housing of the system prior to opening the cassette and removing the imaging plate positioned therein. An advantage of this preferred aspect of the invention is that the cassette is opened within the darkened interior of the housing, thereby avoiding exposing the imaging plate to any unwanted light which may degrade the image.

In preferred aspects, the imaging plate cassette infeed assembly comprises various components including an imaging plate infeed assembly which comprises: (a) a mechanism to pull an imaging plate cassette into the housing; (b) a mechanism to open the imaging plate cassette; and (c) a mechanism to remove an imaging plate from the cassette. After the imaging plate has been scanned and erased (as will be explained) these same mechanisms are operated in reverse order to place the imaging plate back into the cassette, close the cassette and then push the cassette out of the housing. As such, the present cassette "infeed" assembly advantageously operates both as a cassette "infeed" and a cassette "outfeed" assembly.

In preferred aspects, the imaging plate cassette is inserted through a slot in the side of the housing of the device such that a portion of the cassette is positioned within the housing. The cassette infeed assembly is then activated to pull the cassette into the housing. At the end of the scanning and erasing procedures, the cassette (with the imaging plate therein) is re-positioned with a portion sticking out of the slot such that an operator can simply grasp onto the cassette and then pull it fully out of the housing.

In preferred aspects, the mechanism which pulls the imaging plate cassette into the housing (and pushes it out after the imaging plate therein has been scanned and erased) comprises a movable shuttle which holds onto the imaging plate cassette; and a shuttle positioning assembly which moves the shuttle back and forth within the housing. Preferably, the shuttle moves a distance sufficient such that the entire body of the cassette can be pulled into the housing after the shuttle has gripped onto the cassette.

In optional preferred aspects, alignment guides and detent mechanisms are provided (either on one or both of the shuttle and the cassette) to ensure that the cassette is both firmly positioned on the shuttle and correctly centered on the shuttle. An advantage of centering the cassette on the shuttle is that different sized cassettes (each containing different standard or non-standard sized imaging plates) can be used by the present invention. In fact, with no modification being required to the present invention, it can sequentially accept, scan and erase different sized imaging plates (housed in different sized imaging plate cassettes). Furthermore, as will be seen, each of the present scanning and erasing assemblies, and the present imaging plate transportation systems are suited to move different sized imaging plates therethrough, without introducing positioning errors as the imaging plates are moved therethrough.

An imaging plate cassette is a generally flat, plate like structure. In preferred aspects, the scanner which is incorporated into the present system has a low vertical profile (i.e.: it's short), and the imaging plates are slidably moved across the top of a reference plate which covers this scanner in a flat path which passes right on top of the scanner. Accordingly, in preferred aspects, the present invention provides a very compact design with the cassette and the scanner being positioned directly on top of one another. This can be accomplished either by positioning the cassette directly above (or directly below, or side by side) the scanner. In preferred aspects, the scanner used in the present invention is a circular rotating multi-head scanner, offering the advantages of fast scanning within a low vertical profile.

Having such a vertically compact design, the present invention further comprises novel systems for opening the cassette and for pulling the imaging plate out of the cassette, with these operations being performed in a minimal amount of vertical space. In various aspects, novel systems to unlatch (i.e. unlock) the cassette and to open its top cover just enough to pull the imaging plate out, are provided. In one preferred aspect, these systems comprise a claw which is dimensioned to latch onto the top cover of the cassette and pull the top cover open as the shuttle moves the cassette to a final position within the system housing. In one exemplary aspect, this claw is biased upwardly, and moves along a track.

The present invention further comprises a novel curved path erasing assembly which is advantageously positioned between the scanner and the cassette infeed mechanism. In preferred aspects, the erasing assembly comprises a curved structure which flips the imaging plate over as the imaging plate is removed from the cassette and is fed into the scanner.

In various aspects of the invention, the curved structure in the erasing assembly comprises either a curved window (along which the imaging plate slidably passes) or a curved window spaced apart from a curved element (with the imaging plate passing slidably therethrough). As such, the present invention provides a very compact erasing assembly. Being curved, the present erasing assembly considerably reduces the overall size of the present invention. Specifically, by flipping the imaging plate over as it passes therethrough, the present curved erasing assembly permits the infeed path of the cassette into the device to be generally parallel to the path the imaging plate takes across the scanner. Doubling the path through which the imaging plate travels over upon itself in this manner effectively cuts the overall length of the present system in half. Importantly, the present erasing assembly both erases an imaging plate, and guides the imaging plate through the system.

In various aspects, an erasing light source (or sources) may comprise a fluorescent light or a plurality of fluorescent lights or LEDs or a plurality of LED arrays positioned adjacent to (or spaced slightly away from) the curved window, passing erasing light through the curved window, toward the surface of the imaging plate. An advantage of such a curved window design is that the curvature of the window is used to change the direction of travel of the imaging plate while the window permits erasing light to pass therethrough. Specifically, the curved nature of the present erasing system specifically permits the imaging plate to be fed out of the erasing system in a path which is parallel to path in which the imaging plate was fed into the erasing system. Accordingly, a very compact erasing system design is achieved.

In preferred aspects, one or both of the curved window and the curved element positioned adjacent thereto have surfaces which are fabricated from a low friction material. Moreover, in such preferred aspects, various surfaces of the erasing assembly may be at least covered with highly reflective materials thus minimizes light leakage and thereby increases the overall effectiveness of the erasing procedure. Specifically, in these various preferred aspects, a highly reflective surface is disposed around the erasing light source to reflect erasing light through the curved window and onto the surface of the imaging plate sliding thereover.

An advantage of fabricating the curved window (and optional curved element positioned adjacent thereto) from low friction materials is that the imaging plate will slide easily theracross. Preferably, this results in the advantage that it is only necessary to provide a system to feed the imaging plate into one end of the erasing assembly (e.g.: a roller), and a system to extract the imaging plate from the other end of the erasing assembly (e.g.: another roller). As such, it is not necessary to provide a transportation mechanism within the erasing assembly itself to move the imaging plate therethrough.

An advantage of using either fluorescent tube lighting or LED erasing lights in the erasing assembly (especially when also using highly reflective coatings within the erasing assembly) is that the entire erasing assembly need only comprise a short structure relative to the overall length of the imaging plate passing therethrough. Stated another way, only a portion of the imaging plate need be disposed adjacent to the erasing assembly at any time. As such, a "middle band" of the imaging plate can be passing through the erasing assembly at the same time that the proximal end distal ends of the imaging plate extend out of the erasing assembly. In contrast, many existing erasing systems are much larger and the entire imaging plate must be positioned within an erasing "chamber" such that the entire imaging plate is erased (by turning on erasing lights in the chamber) at the same time.

As such, it is not necessary for the present invention to provide a transportation mechanism within the erasing assembly itself, or to first position the entire imaging plate within the erasing section of the device and then later remove the imaging plate. Rather, in accordance with the present invention, movement of the imaging plate can be controlled without a transportation mechanism within the erasing assembly itself since at least one end of the imaging plate will protrude from the erasing assembly at all times. This protruding end or ends can easily be grabbed by a roller, etc. at either the infeed or the outfeed end of the erasing assembly.

In optional preferred aspects, the erasing light(s) of the present erasing system are positioned around the outer (convex) surface of the curved window. An advantage of erasing around the outer surface of the curved window (as compared to erasing around the inner surface of the curved window) is that the outer surface is longer than the inner surface, yielding a greater distance over which the erasing can be carried out. Also, more physical space is available for positioning multiple erasing light sources theraround.

An imaging plate transportation assembly is provided to move the imaging plate back and forth in a path extending from the imaging plate cassette, past the erasing assembly and past the scan area adjacent to the scanner. Specifically, and in accordance with the preferred method, the imaging plate is fed into the device until it reaches a position at which it is stopped, and its direction of travel is reversed, passing by the scanner and then through the erasing assembly. As such, the present method specifically provides that the imaging plate is first moved fully into the device, stopped, and then is sequentially scanned and erased while being withdrawn. It is be understood, however, that the present invention also encompasses those applications in which the imaging plate is scanned prior to its direction of travel being reversed (such that it is scanned while being inserted, stopped, and then erased while being withdrawn from the device).

In preferred aspects, the scanner comprises a multi-head scanner, and more preferably a rotating multi-head scanner, and most preferably a rotating three-head scanner. However, it is to be understood that the present scanning system is not so limited.

In one preferred aspect of the invention, the scanner is covered by a reference plate and the imaging plate is slid across the reference plate (passing through a scan area therealong). Preferably, the imaging plate is moved across the surface of this reference plate by a belt roller or other device which firmly positions the imaging plate against the reference plate. In preferred aspects, a center portion of the belt (between two rollers suspending the belt) is biased directly against the reference plate.

In preferred aspects the reference plate has a slot passing therethrough and the scanning head(s) of the scanner move along the slot such that light from the scanning head is directed across the imaging plate as the scanning head is moved along the slot. In most preferred aspects, a rotary scanner is used. Accordingly, in these preferred aspects, the slot in the reference plate is also curved.

An advantage of this system is that, by positioning the imaging plate firmly against the reference plate which covers the scanner, a very good light-tight seal is maintained at the scan area where the imaging plate is actually scanned. An important advantage of maintaining such a very good light-tight seal at this location is that it avoids the need for a light filter between the erasing and scanning portions of the present invention. Thus, the erasing assembly can be positioned very close to the scanning assembly.

A further advantage of the present novel system of slidably moving the imaging plate across a reference plate which covers the scanner is that the imaging plate is maintained at a known (small) distance from the scanning heads passing across thereunder. As this separation distance between the imaging plate and the scanning heads remains constant (both as the imaging plate is moved across the reference plate of the scanner and as the scanning heads are rotated such that a scanning beam passes across the surface of the imaging plate) it is possible to advantageously focus the laser beam from the scanning heads into a small spot on the imaging plate (thus achieving constant laser spot size on the imaging plate). This advantage is particularly beneficial when reading the image on the imaging plate as uneven spot size results in unwanted image artifacts on the final (on screen) image. A further benefit of the present preferred scanning system is that the angle of the scanning laser beams with respect to the imaging plate remains constant as the scanner's scanning heads pass across the surface of the imaging plate.

In accordance with the present system, a preferred method of scanning and then erasing an imaging plate with a combined imaging plate scanning and erasing system is also provided. This method may preferably comprise: (a) inserting an imaging plate cassette into the combined imaging plate scanning and erasing system, wherein the imaging plate is stored within the imaging plate cassette; (b) pulling the imaging plate cassette into the combined imaging plate scanning and erasing system; (c) opening the imaging plate cassette; (d) removing the imaging plate from the imaging plate cassette; (e) moving the imaging plate in a path extending past a curved erasing assembly and then through a scan area adjacent to a scanner; (f) scanning an image on the imaging plate with the scanner; (g) moving the imaging plate back through the scan area and then back past the erasing assembly; (h) erasing the imaging plate with the erasing assembly; (i) placing the imaging plate back into the imaging plate cassette; (j) closing the imaging plate cassette; and (k) pushing the imaging plate cassette out of the combined imaging plate scanning and erasing system.

In preferred aspects, the imaging plate is removed from the cassette (preferably after at least a portion of the cassette has been pulled within the housing of the system). Thereafter, the imaging plate is first moved through the erasing assembly then passing at least partially across the scanner. (In particular, the imaging plate is preferably passed through a scan area adjacent to a reference plate which covers the scanner).

In most preferred aspects, the imaging plate is moved a distance such that its distal end passes fully across the scan area (and across the scanner) and is positioned in an outfeed area distal to the scanner. Thereafter, the imaging plate is moved in an opposite direction, moving back across the surface of the reference plate covering the scanner, passing through the scan area, at which time it is then scanned. After passing across the scanner, the imaging plate then passes back through the erasing assembly, at which time any residual images or image artifacts are erased by the erasing system (which is only then turned on).

In an additional erase only mode of operation, the present system can be used to erase imaging plates without first reading them. This is a standard recommended practice prior to exposing imaging plates when they have been sitting idle for an extended period. In such cases the plates can pick up noise artifacts due to background radiation including cosmic rays. In this mode, the erase lights can be illuminated continuously both during the in feed direction and the out feed direction of imaging plate motion. This has the benefit of slightly reducing the time required to complete an erase cycle.

In the preferred aspect of the invention in which a multiple-head rotary scanner is used (and in which successive scanning heads pass along a curved slot in a reference plate covering the scanner) the imaging plate is first advanced to a position such that its proximal edge passes fully past a curved slot in the reference plate. At this position, a distal portion of the imaging plate will be received within the outfeed area while a portion of the imaging plate remains positioned on top of the scanner. As will be explained, an advantage of this design is that the outfeed area need even not be as long as the imaging plate. In preferred aspects, the outfeed area is itself curved downwardly in front of the scanner, further saving space in the present design.

An advantage of using a single friction belt drive to slide the imaging plate over the surface of the reference plate covering the scanner is that this avoids image artifacts caused by speed variation and hand-off errors which may instead occur in the case of multiple driving elements.

A further advantage of the present curved path erasing system comprising a curved window spaced apart from a curved member is that each of these curved elements can be attached to separate components of the system such that when the present device is opened, these two portions of the eraser assembly move apart, permitting easy access to an image plate which has become jammed in between.

It is a further advantage of the present system that the scanner and the erasing assembly can be positioned close enough together such that portions of the imaging plate can be erased at the same time as other portions of the imaging plate are being scanned.

Being very compact, the present device is portable and may be moved room-to-room in a hospital or laboratory setting. In contrast, all known existing systems are large floor standing devices, typically the size of a large refrigerator.

BRIEF DESCRIPTION OF THE DRAWINGS

FIG. 1 is a schematic side elevation view of the present invention, before an operator has inserted an imaging plate cassette therein.

FIG. 2 is a schematic side elevation view corresponding to FIG. 1 after the operator has inserted the imaging plate cassette into the invention, with the cassette interlocking with the shuttle.

FIG. 3 is a view corresponding to FIG. 2, after the shuttle has been moved to pull the cassette into the device, showing the cassette positioned over top of the scanner.

FIG. 4 is a view corresponding to FIG. 3, after the cassette has been opened, showing the imaging plate being removed from the cassette and passing through the erasing assembly.

FIG. 5 is a view corresponding to FIG. 4, but with the imaging plate positioned such that a distal end of the imaging plate is within a curved outfeed area distal to the scanner.

DETAILED DESCRIPTION OF THE DRAWINGS (a) Major System Components and Preferred Method of Operation:

The present invention provides a combined imaging plate scanning and erasing system which advantageously scans and then erases an imaging plate within a single device which takes up only a very small amount of space.

FIGS. 1 to 5 show sequential steps in operating the present invention in accordance with a preferred method.

Figure 1:
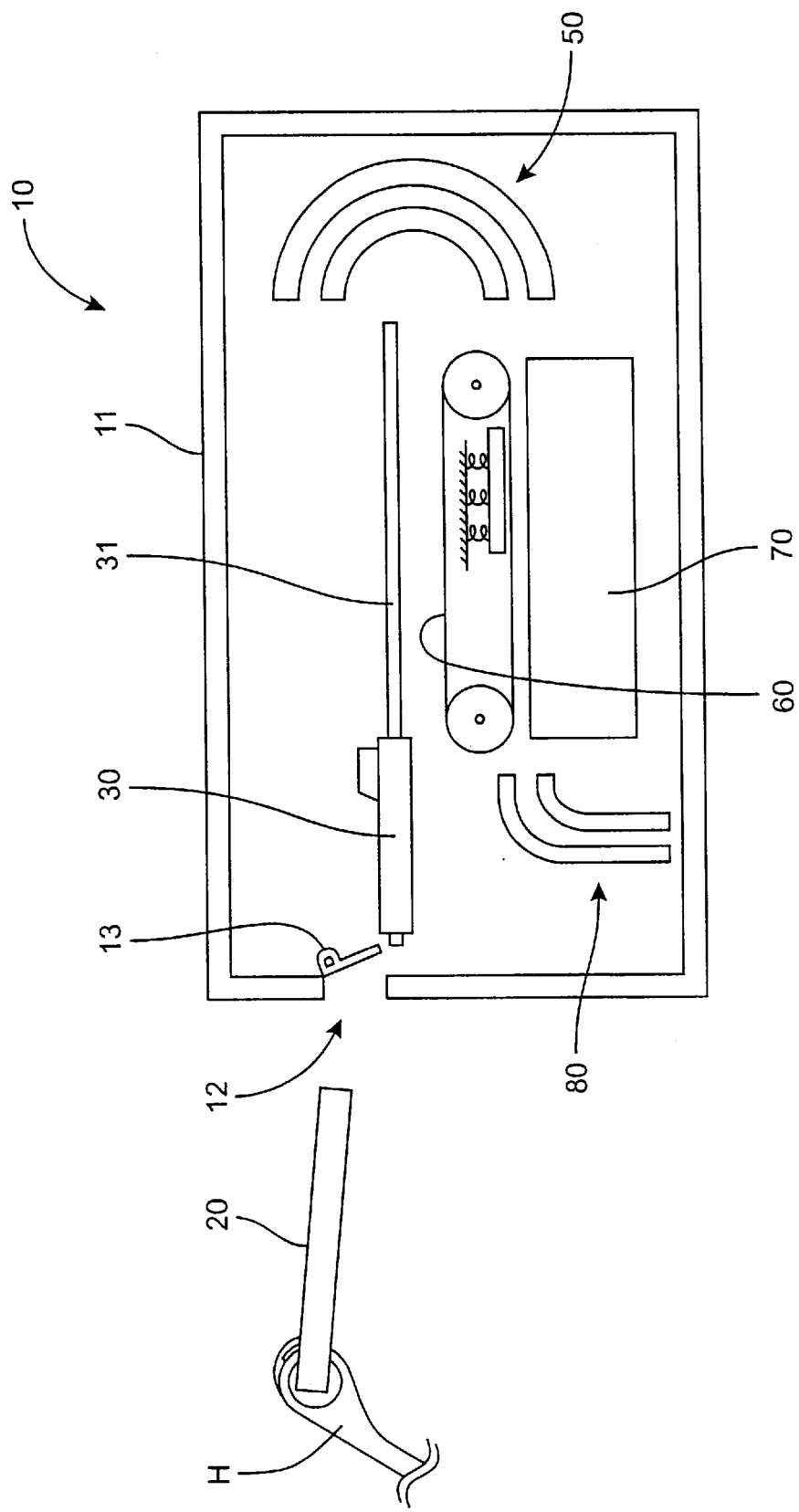
FIGS. 1 to 5 show sequential steps in operating the device of the present invention in accordance with a preferred method. As will be explained, the steps shown in FIGS. 1 to 5 are carried sequentially to position the imaging plate prior to scanning and are then reversed as the imaging plate is scanned and is then erased. (Optionally, however, the imaging plate may be scanned while being moved from the position of FIG. 4 to that of FIG. 5).

Referring first to FIG. 1, a combined imaging plate scanning and erasing system 10 having a housing 11 is provided. A hand H of a human operator is shown holding an imaging plate cassette 20 prior to scanning (i.e.: prior to reading an image stored thereon) and then erasing an imaging plate. Housing 11 has a slot 12 through which the operator inserts cassette 20.

Figure 2:
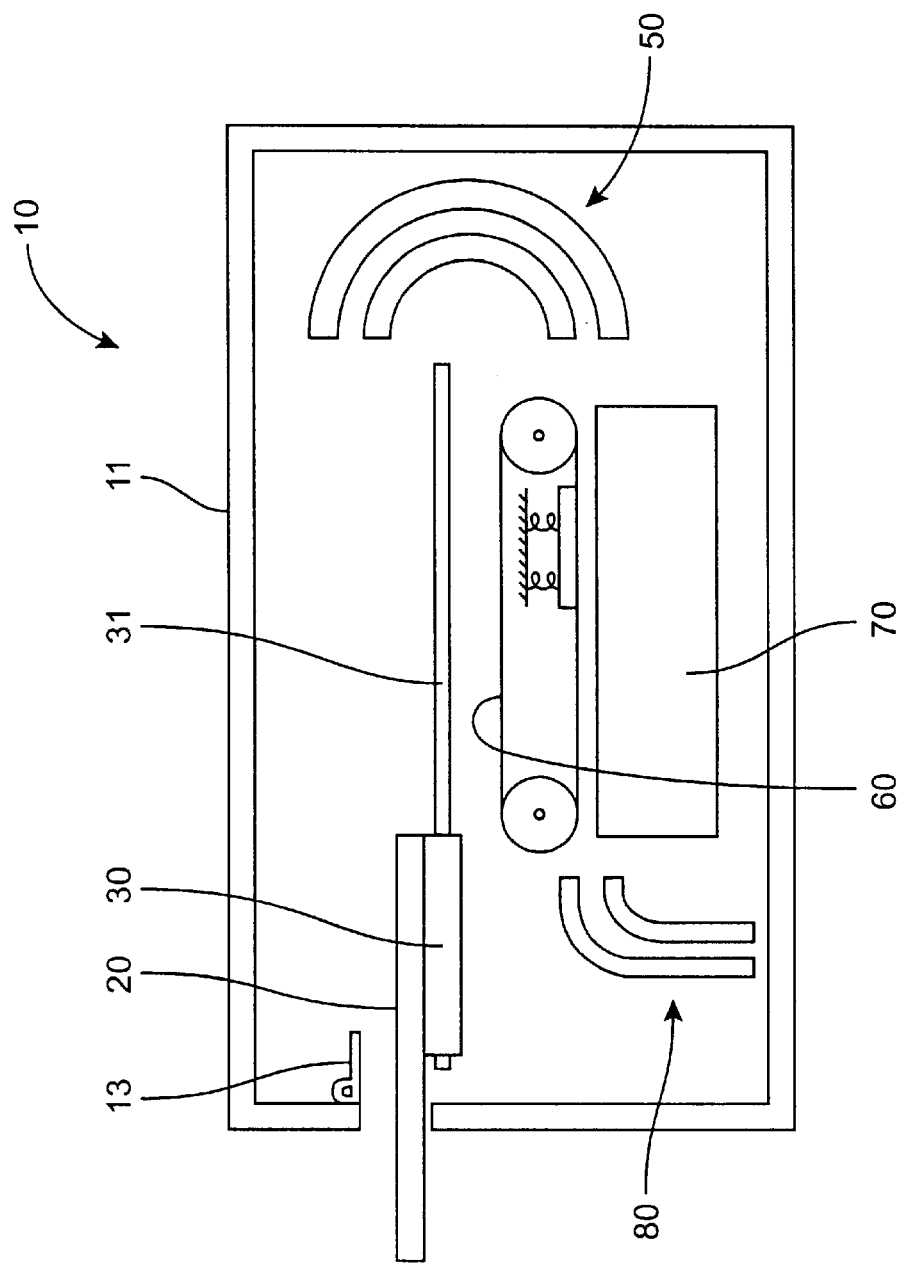

As shown in FIG. 2, cassette 20 is preferably positioned by the operator such that at least a portion of cassette 20 is positioned within housing 11. As will be explained in further detail herein, a movable shuttle 30 is positioned to securely grab or latch onto cassette 20.

Figure 3:
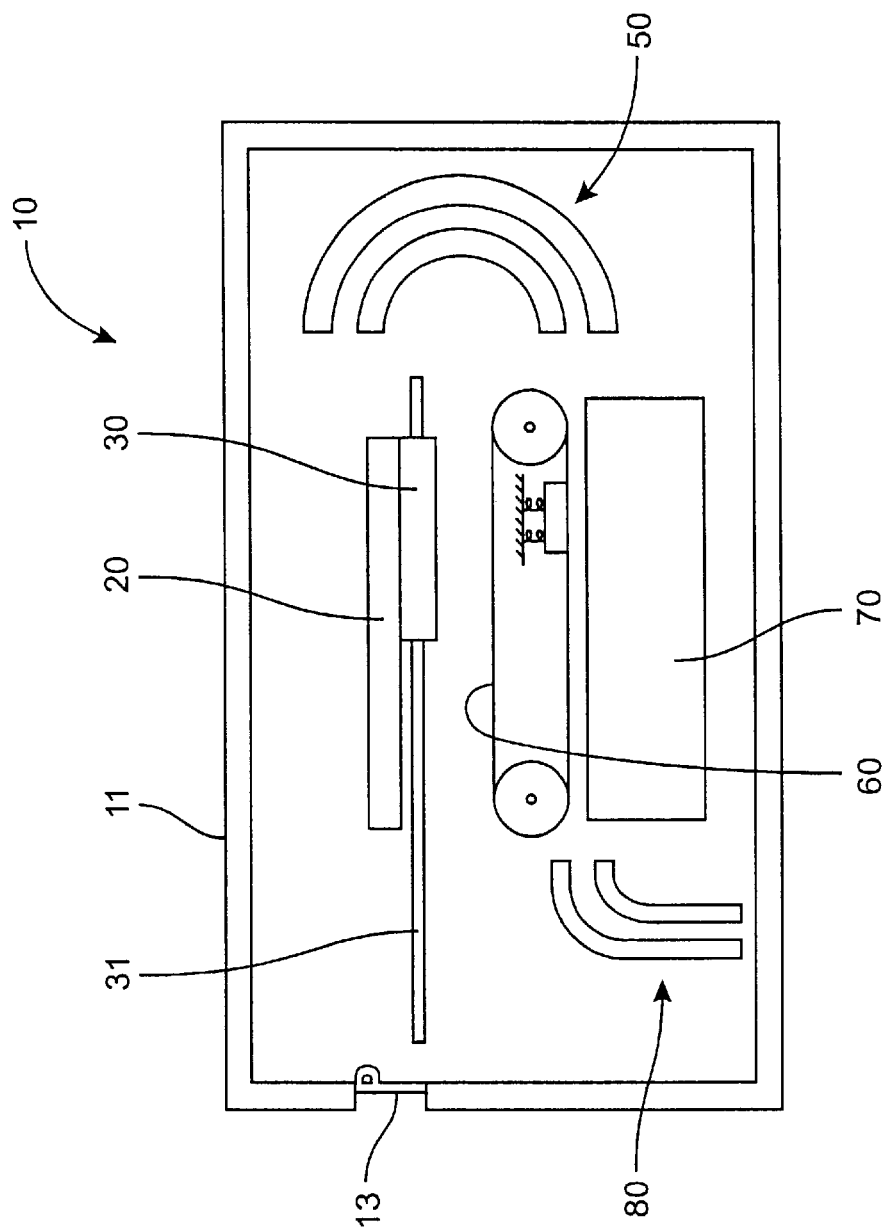

A shuttle positioning assembly 31 then moves shuttle 30 (and cassette 20 held thereon) to the position shown in FIG. 3. At this time, a door 13 closes slot 12 in housing 11 such that light is prevented from entering the interior of housing 11. Together, shuttle 30 and shuttle positioning assembly 31 thus comprise a mechanism for pulling cassette 20 into housing 11.

Figure 4:
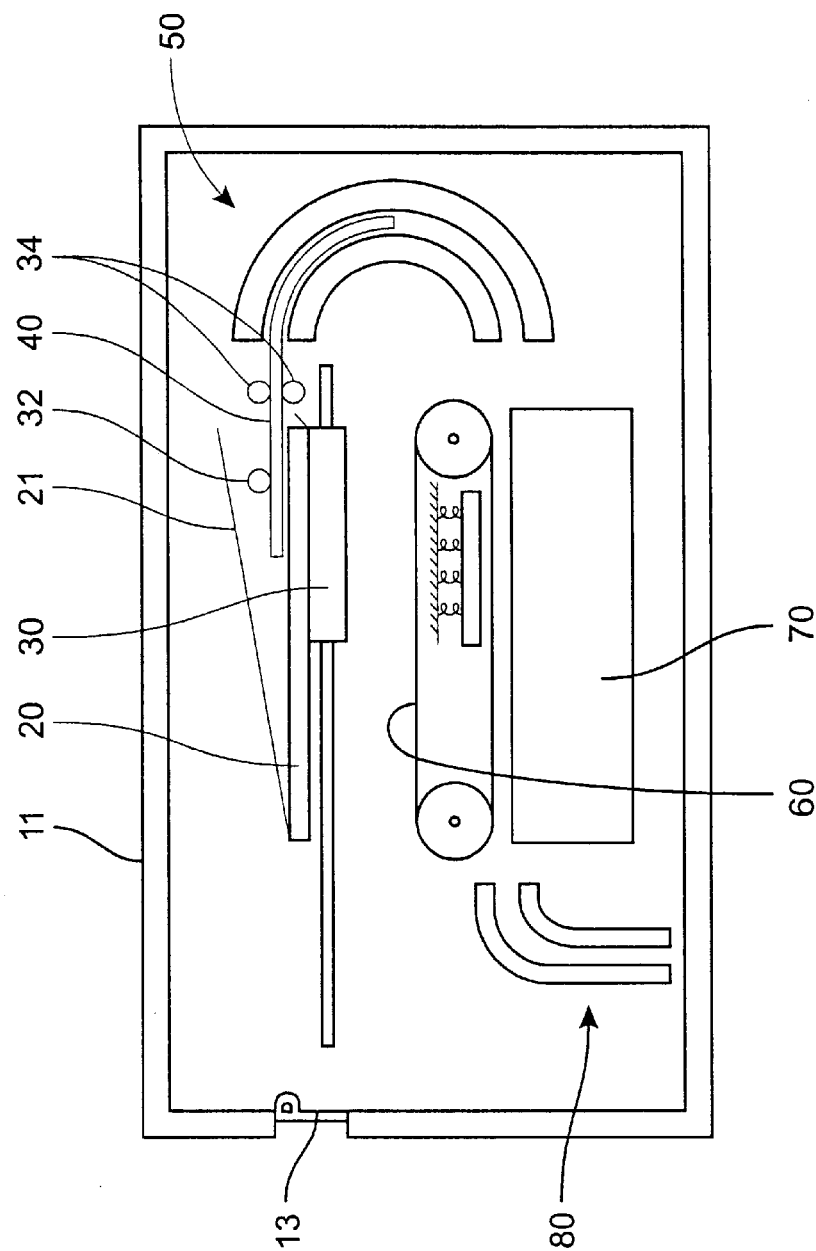
Figure 16:
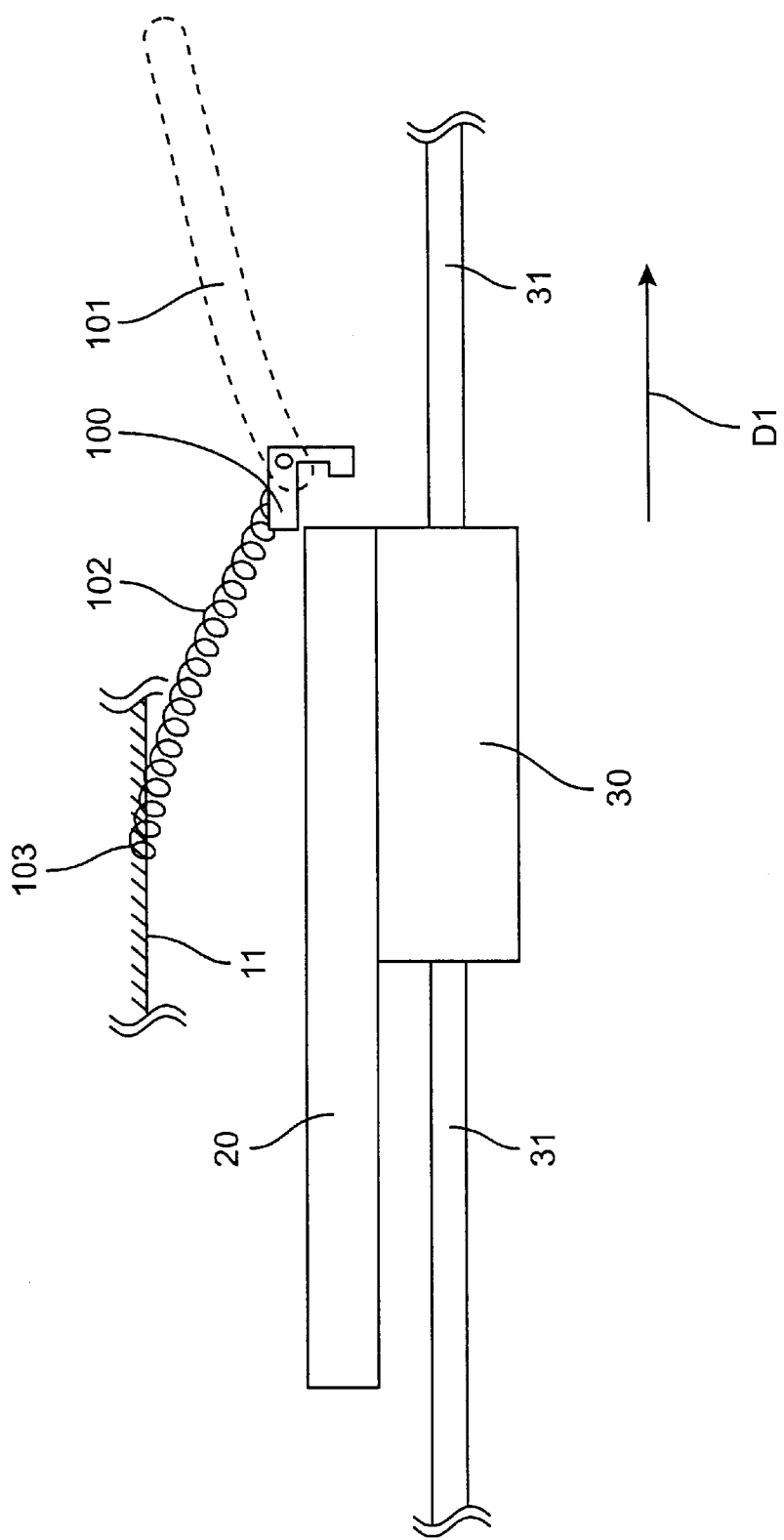
FIG. 16 is a schematic side elevation view of a mechanism for opening a top cover on the cassette (prior to opening the cassette).
Figure 17:
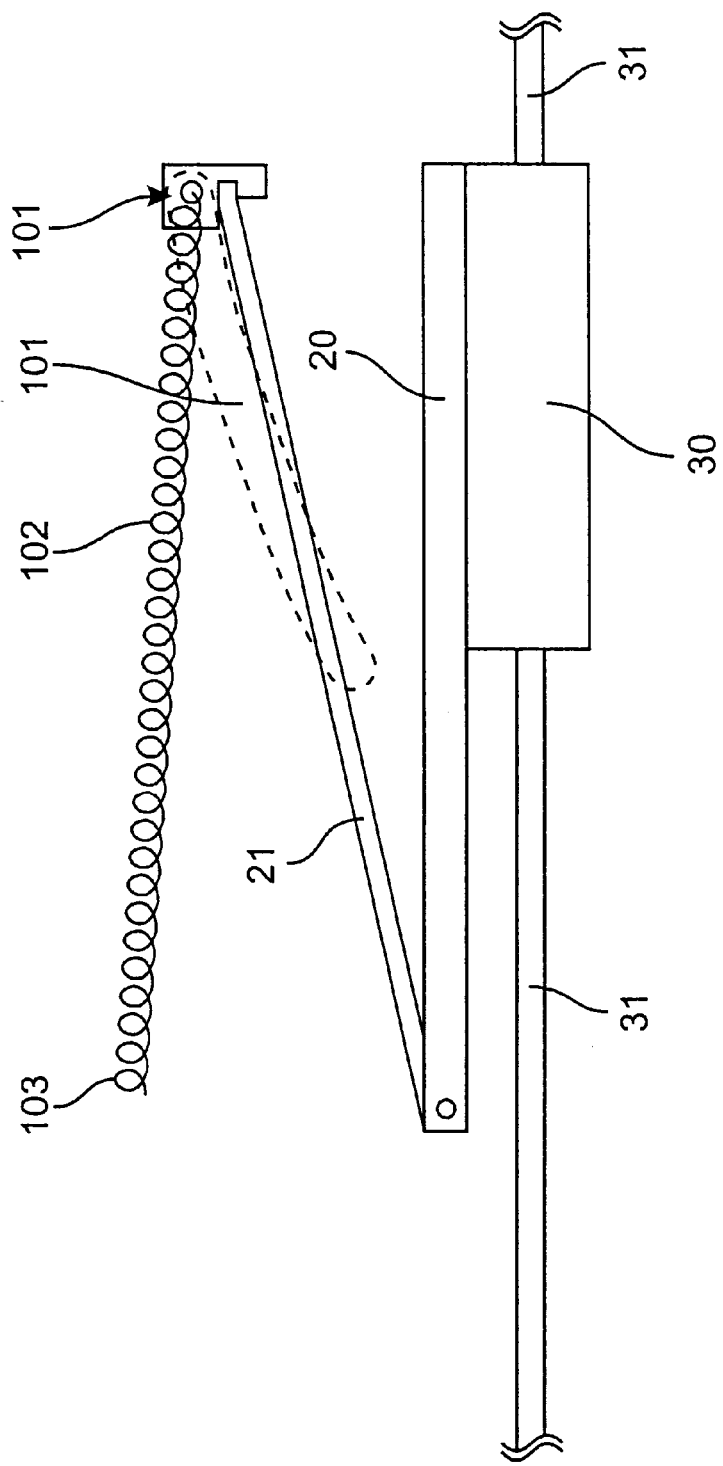
FIG. 17 is a schematic side elevation view of a mechanism for opening a top cover on the cassette (after opening the cassette).

As shown in FIG. 4, the top cover 21 of cassette 20 is opened when shuttle 30 has moved cassette to its final position within housing 11. As such, top cover 21 of cassette 20 is in its final open position. (Further details of a preferred mechanism to open top cover 21 of cassette 20 are shown in FIGS. 16 and 17, explained below.) Also provided is a mechanism to remove imaging plate 40 from cassette 20. In this regard, a grab roller 32 is provided to pull imaging plate 40 out of cassette 20 and a pair of pinch rollers 34 are provided to move imaging plate 40 such that it can then be advanced through erasing assembly 50.

Figure 5:
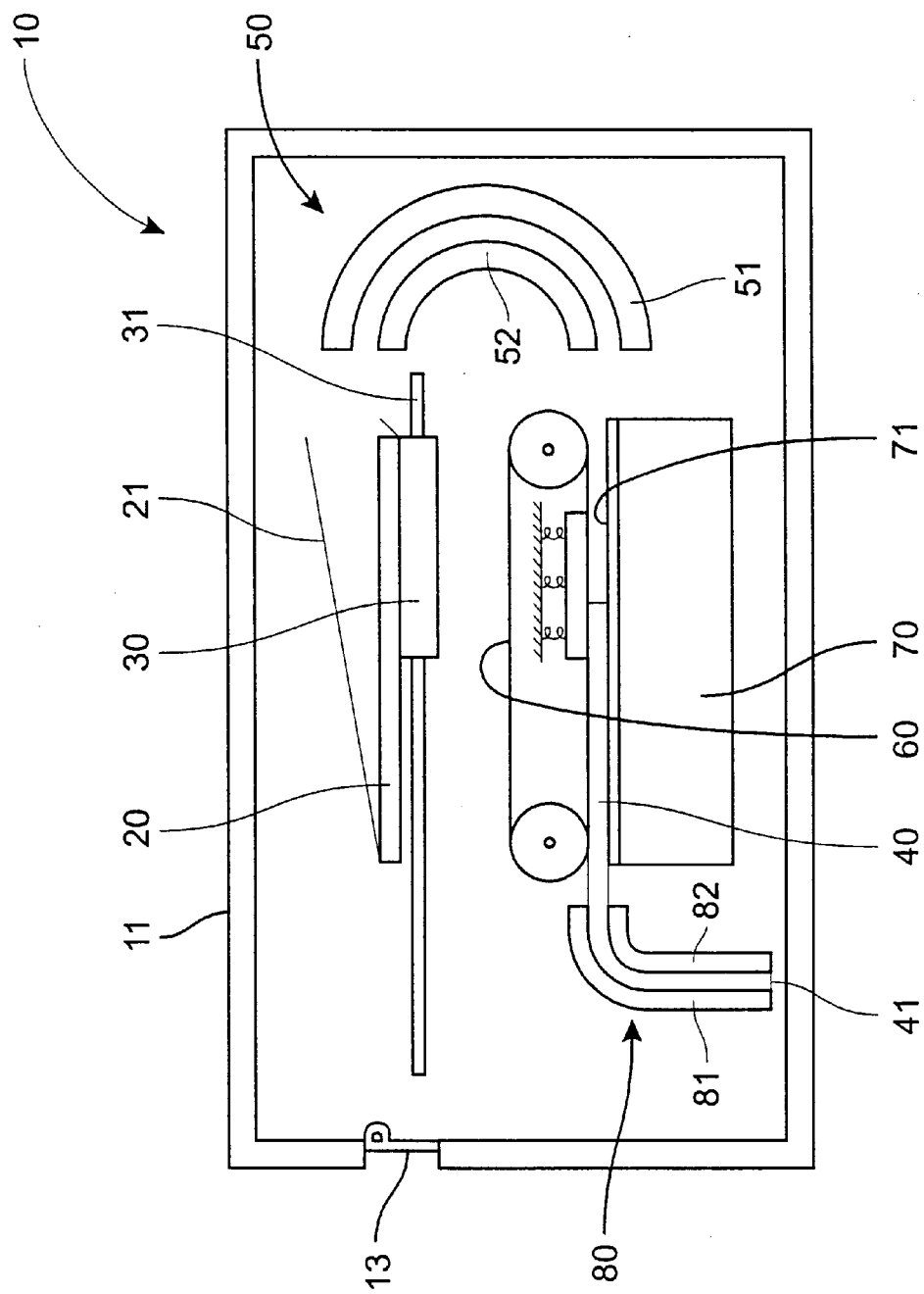

As shown in FIG. 5, imaging plate 40 is then passed through erasing assembly 50, and is then grabbed by friction belt roller 60 and is slid across a reference plate 71 which covers scanner 70. Friction belt roller 60 moves imaging plate 20 to a final position at which the distal end 41 of imaging plate 40 is positioned within a curved outfeed area 80. Outfeed area 80 may optionally comprise a pair of guides 81 and 82.

After imaging plate 40 is positioned as shown in FIG. 5, it can then be scanned by reversing its direction of travel, (ie: passing imaging plate 40 back across the surface of scanner 70, or, more preferably, across the surface of reference plate 71 which covers scanner 70). Thereafter, imaging plate 40 is moved back through erasing assembly 50 which advantageously erases any latent images or image artifacts in imaging plate 40.

It is to be understood that imaging plate 40 can be scanned by scanner 70 either as it initially passes distally across scanner 70. However, in a more preferred aspect, imaging plate 40 is scanned by scanner 70 after it has been fully distally advanced into the system (i.e.: passing at least partially into outfeed area 80), stopped, and its direction of travel has been reversed such that it is passing back towards cassette 20 when being scanned.

As illustrated, cassette 20 is received into housing 11 and positioned directly above scanner 70. It is to be understood that, housing 11 could alternatively be positioned directly under scanner 70 instead.

As can be seen the path cassette 20 moves back and forth in housing 11 is preferably generally parallel to the path imaging plate 40 travels across scanner 70. Being curved, erasing assembly 50 turns imaging plate 40 around (by flipping it over) in a small space, minimizing the size of housing 11.

As can also be seen, device 10 is small enough such that a portion of imaging plate 40 can be passing across scanner 70 at the same time that another portion of imaging plate 40 can be passing through curved erasing assembly 50.

(b) Erasing Assembly:

Further details of various preferred embodiments of erasing assembly 50 are shown in FIGS. 6A to 8. In preferred aspects, erasing assembly 50 comprises a curved window 51. By sliding imaging plate 20 against curved window 51 (as shown in the sequence of FIGS. 1 to 5) imaging plate 40 is flipped over from the orientation in which it was placed in cassette 20 to the orientation in which it is presented to scanner 70.

To further guide the passage of imaging plate 40 through erasing assembly 50, a curved member 52 may be positioned adjacent to curved window 51, thus providing a narrow passageway for an imaging plate to pass therebetween. In preferred aspects, the spacing between curved window 51 and curved member 52 may be on the order of 0.100 to 0.150 inches (i.e.: just sufficiently wide enough for imaging plate 40 to pass therebetween).

In optional aspects, surface 55 of curved member 52 can be covered by, or fabricated from, a low friction material (to ease sliding of imaging plate 40 thereover). In preferred aspects, this low friction material may optionally be selected from the group consisting of acrylic, polycarbonate, glass, zinc coated steel and electroless nickel with Teflon impregnation.

In other optional aspects, surface 55 of curved member 52 can be covered by, or fabricated from, a highly reflective backing surface (disposed on the side of the window opposite the at least one erasing light source). Accordingly, when imaging plate 40 occupies a portion of the area exposed by window 51, the remainder of the area exposed by window 51 exposes some portion of the highly reflective backing surface 55.

In addition, window 51 may itself be fabricated from (or covered by) a low friction material, including, but not limited to acrylic, polycarbonate or glass.

Figure 7:
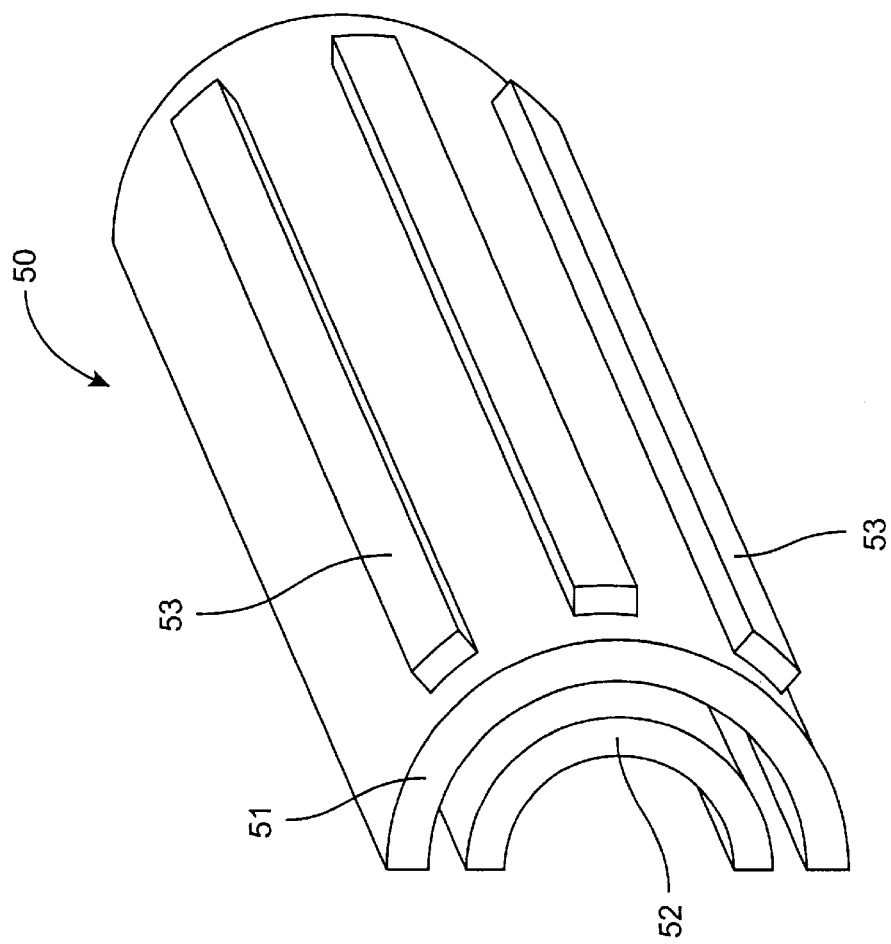
FIG. 7 is a perspective view corresponding to FIG. 6A.

Preferably, curved window 51 has one or more erasing lights 53 positioned therearound. Any suitable form of erasing light is considered. In one preferred aspect, lights 53 may comprise may comprise arrays of LEDs (positioned at spaced apart intervals around the circumference of curved window 51 as shown in FIG. 7). In an alternate preferred aspect, lights 53 may be mounted on a single board fabricated to conform to the shapes of 51 and 59. For example, by using a flexible circuit board that can be bent to a matching curved shape.

Figure 6A:
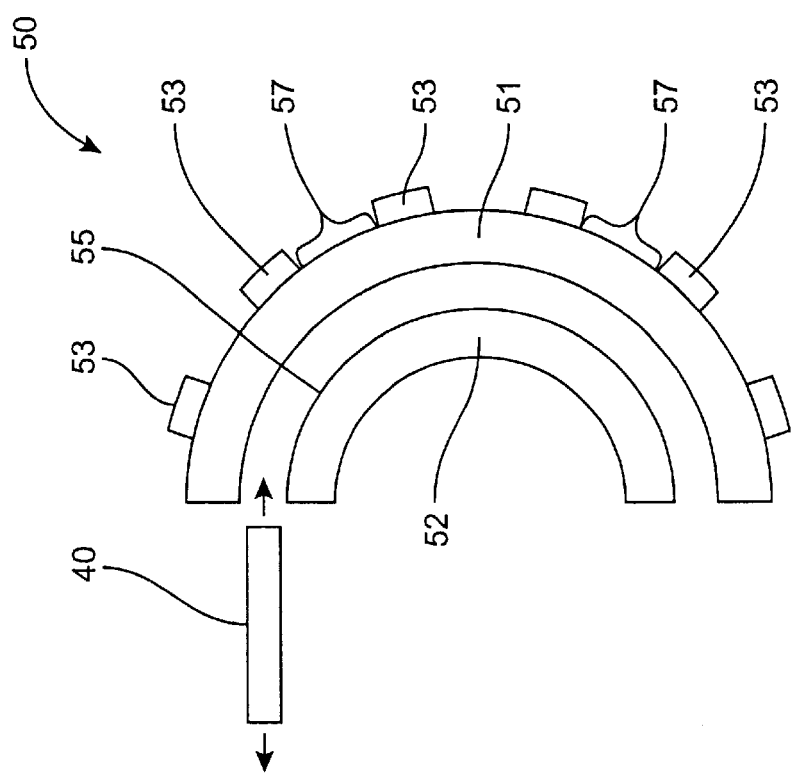
FIG. 6A is a schematic side elevation view of one embodiment of the erasing assembly of the present invention.

In addition, as shown in FIG. 6A, all or part of the outside surface 57 of window 51 (i.e.: some or all of the regions between successive lights 53) may also be covered by, or fabricated from, a material which is highly reflective. This highly reflective coating would ensure that erasing light (emitted from lights 53) which is then reflected off the surface of imaging pate 40 is then re-directed towards the surface of imaging plate 40. Thus, ensuring a highly reflective surface 57 ensures that light is reflected back and forth through curved window 51, increasing erasing effectiveness. In various aspects, the highly reflective portions of the outside surface 57 of window 51 may be disposed between arrays of erasing lights, or may be disposed between the individual erasing lights in the arrays, or both.

Figure 6B:
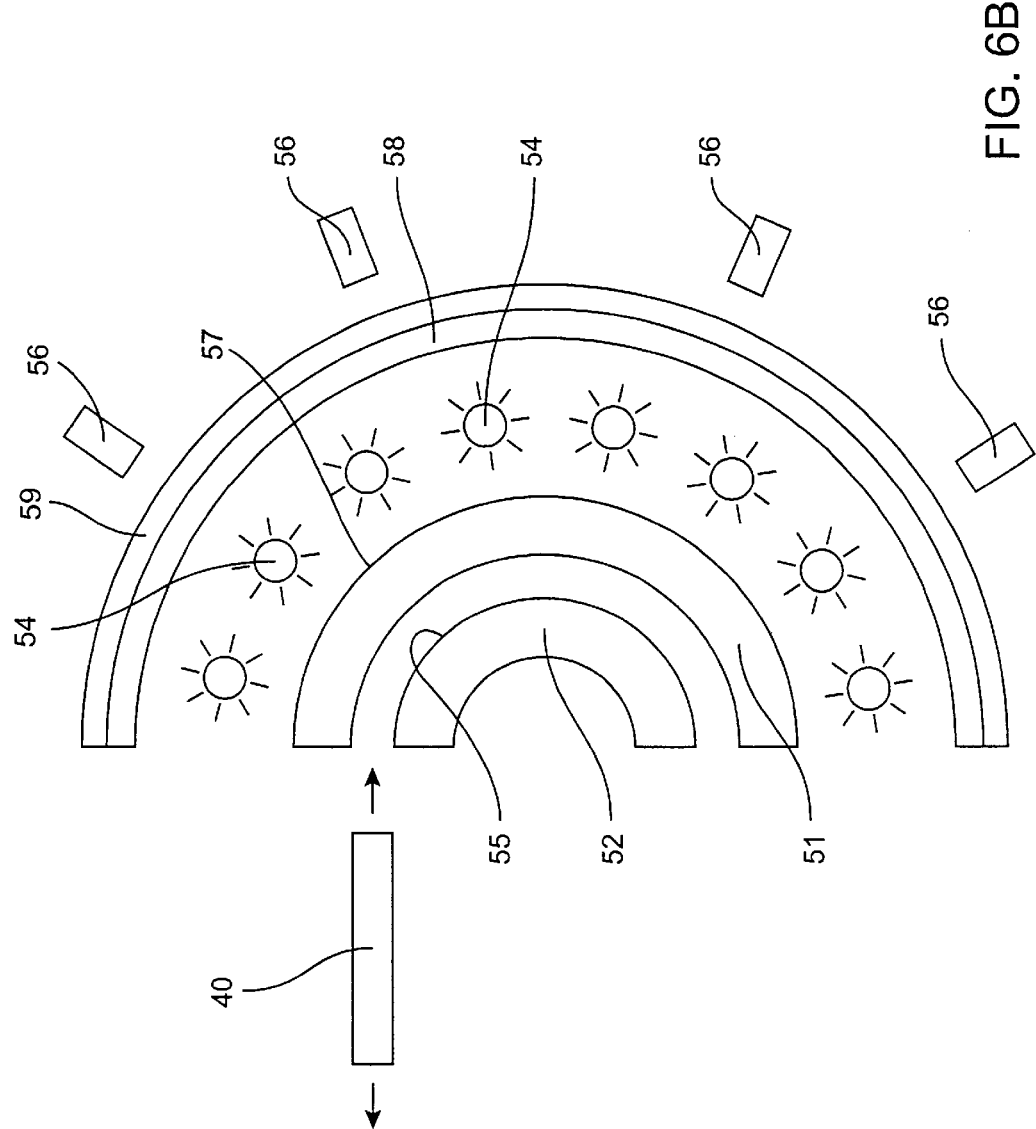
FIG. 6B is a schematic side elevation view of another embodiment of the erasing assembly of the present invention.

Alternatively, as shown in FIG. 6B, a plurality of erasing lights 54 (which are spaced farther from window 51) may instead be used. Erasing lamps 54 preferably comprise fluorescent tubes, however, any suitable erasing lamp (including, but not limited to, gas discharge lamps, Na lamps, Ne lamps, metal halide lamps and Xe lamp) may be used. Florescent erasing lights 54 may also be positioned spaced apart intervals around the circumference of curved window 51 similar to lights 53 in FIG. 7). In this case, a highly reflective surface 58 is preferably disposed around lights 54. In preferred aspects, florescent erasing lights 54 are spaced apart by at least 1.2 times the diameter of the fluorescent tubes thereby allowing light from the back side of the fluorescent tubes to reach imaging plate 40.

Erasing lights 53 or 54 are thus positioned to direct erasing light through window 51. Being positioned on the opposite side of window 51 to which imaging plate 20 passes, lights 53 can optionally be positioned very close to imaging plate 40, without interfering with the motion of imaging plate 40 as it slides thereover.

The highly reflective material used on surface 57 or 58 may, in preferred aspects, comprise a mirror, white paint, white silkscreen or white or aluminized plastic. However, any suitable highly reflective material is contemplated within the scope of the present invention.

It is to be understood that in the case where erasing light is generated by lights 54, surface 57 of curved window 51 is preferably either covered with a one-way mirror or is not covered by any reflective coating (such that surface 57 does not simply reflect erasing light back towards lights 54, but instead directs light through curved window 51 towards the surface of imaging plate 40).

In preferred aspects, erasing lights 53 (which may comprise LEDs) or 54 (which may comprise fluorescent tubes, including hot or cold cathode fluorescent tubes) preferably emit a wide spectrum of white visible light to erase imaging plate 40.

As is also shown in FIG. 6B, a thermal blanket 59 may be wrapped around the element comprising surface 58, and/or heating elements 56 may optionally be provided to keep fluorescent tubes 54 warm such that they can be quickly turned on to a desired intensity to erase imaging plate 40. (Lights 54 must be kept turned off when imaging plate 40 is initially advanced through erasing assembly 50 prior to scanning.

Figure 8:
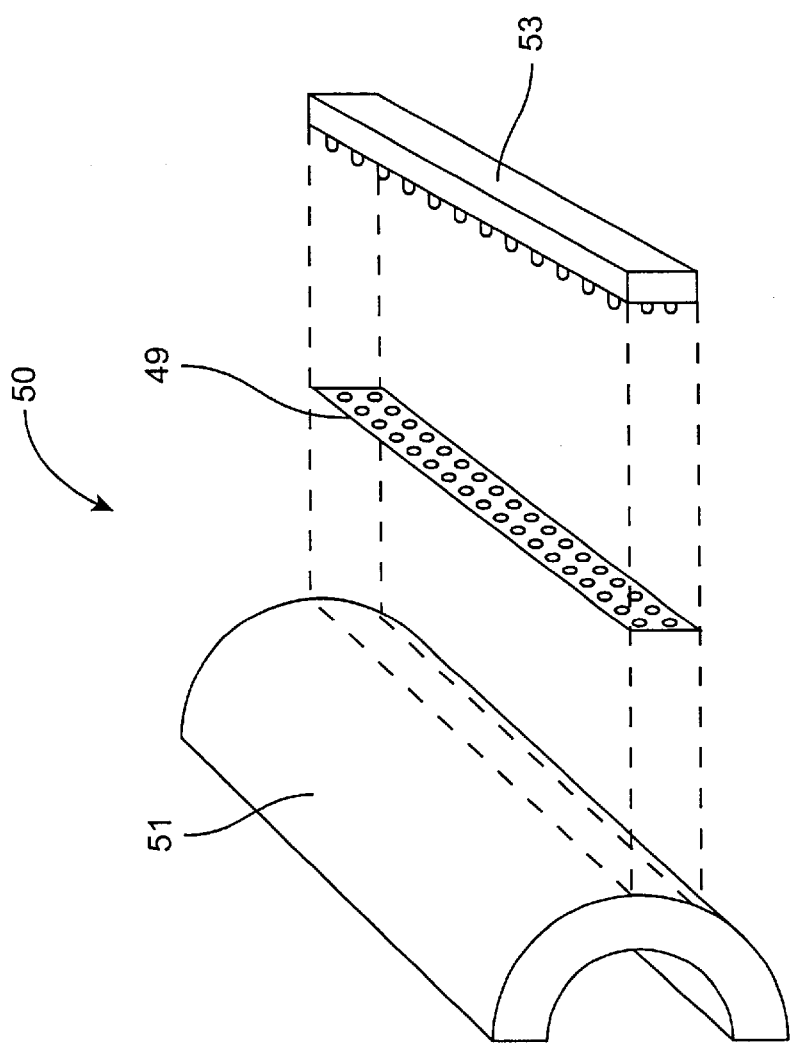
FIG. 8 is an exploded view of an optional preferred aspect of the erasing assembly.

A further optional aspect of erasing assembly 50 is shown in FIG. 8, in which each of lights 53 comprise an array of LEDs. In this optional aspect, a member 49 having a plurality of holes passing therethrough is positioned between window 51 and array of lights 53. The surface of member 56 which is positioned against window 51 is preferably made of a highly reflective material, with the individual holes passing through member 56 aligning with the individual light sources in light array 53. Accordingly, the spaces between each of the individual lights in light array 35 will be highly reflective such that light reflected off the surface of imaging plate 40 will be reflected again thereon.

Figure 6C:
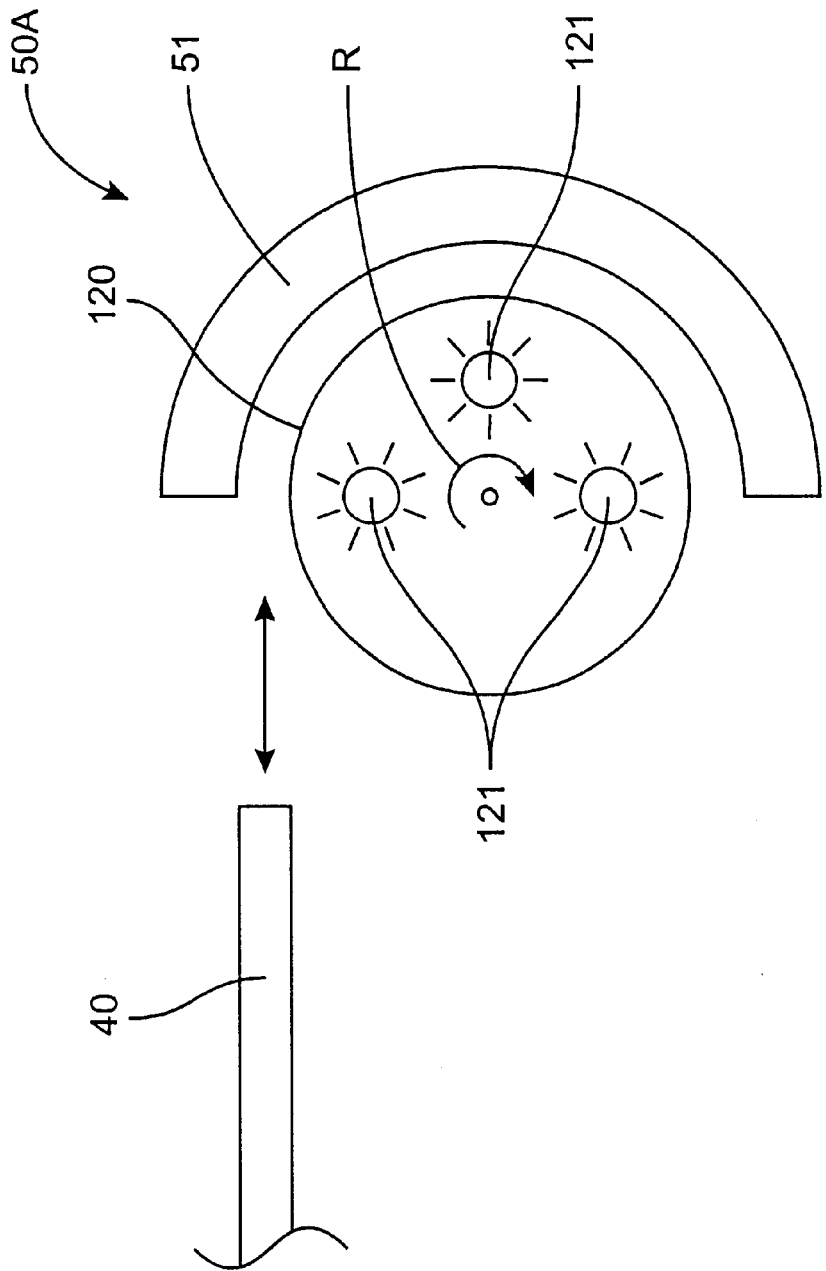
FIG. 6C is a schematic side elevation view of yet another embodiment of the erasing assembly of the present invention.

In yet another alternative embodiment of the erasing assembly 50A, shown in FIG. 6C, a light transmissive drum 120 having at least one erasing light 121 therein is used to erase imaging plate 40. Optionally, light transmissive drum 120 may be rotated such that it pulls imaging plate 40 through erasing assembly 50A.

It is also to be understood that the present erasing assembly can be modified such that erasing is carried out on the interior of the curve of the curved erasing assembly. An example is shown in FIG. 6D in which erasing light 54 erases imaging plate 40 as it passes between window 51 and curved member 52.

Figure 6D:
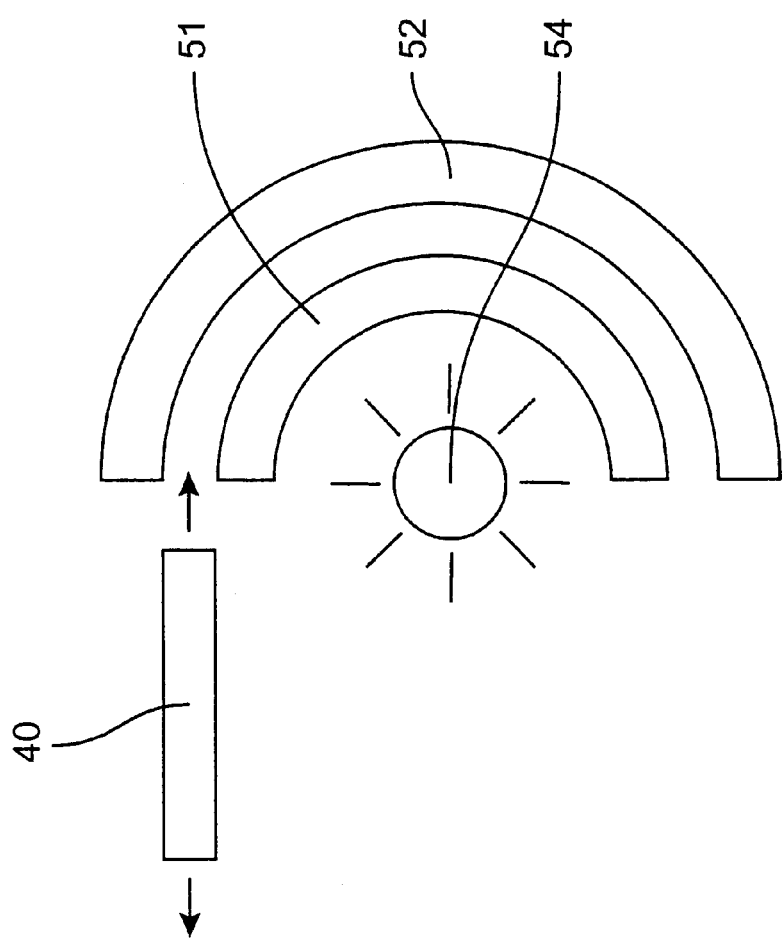
FIG. 6D is a schematic side elevation view of yet another embodiment of the erasing assembly of the present invention.

In both the embodiments shown in FIGS. 6C and 6D, the top/bottom orientation of imaging plate 40 is reversed from that of FIGS. 6A, 6B, 7 and 8. In such cases, the orientation of the scanner assembly is preferably reversed. (i.e.: In the embodiments shown in FIGS. 6C and 6D, it may be preferably to pass imaging plate 40 under scanner 70 with scanner 70 being flipped over from the orientation shown in FIGS. 1 to 5).

Figure 9:
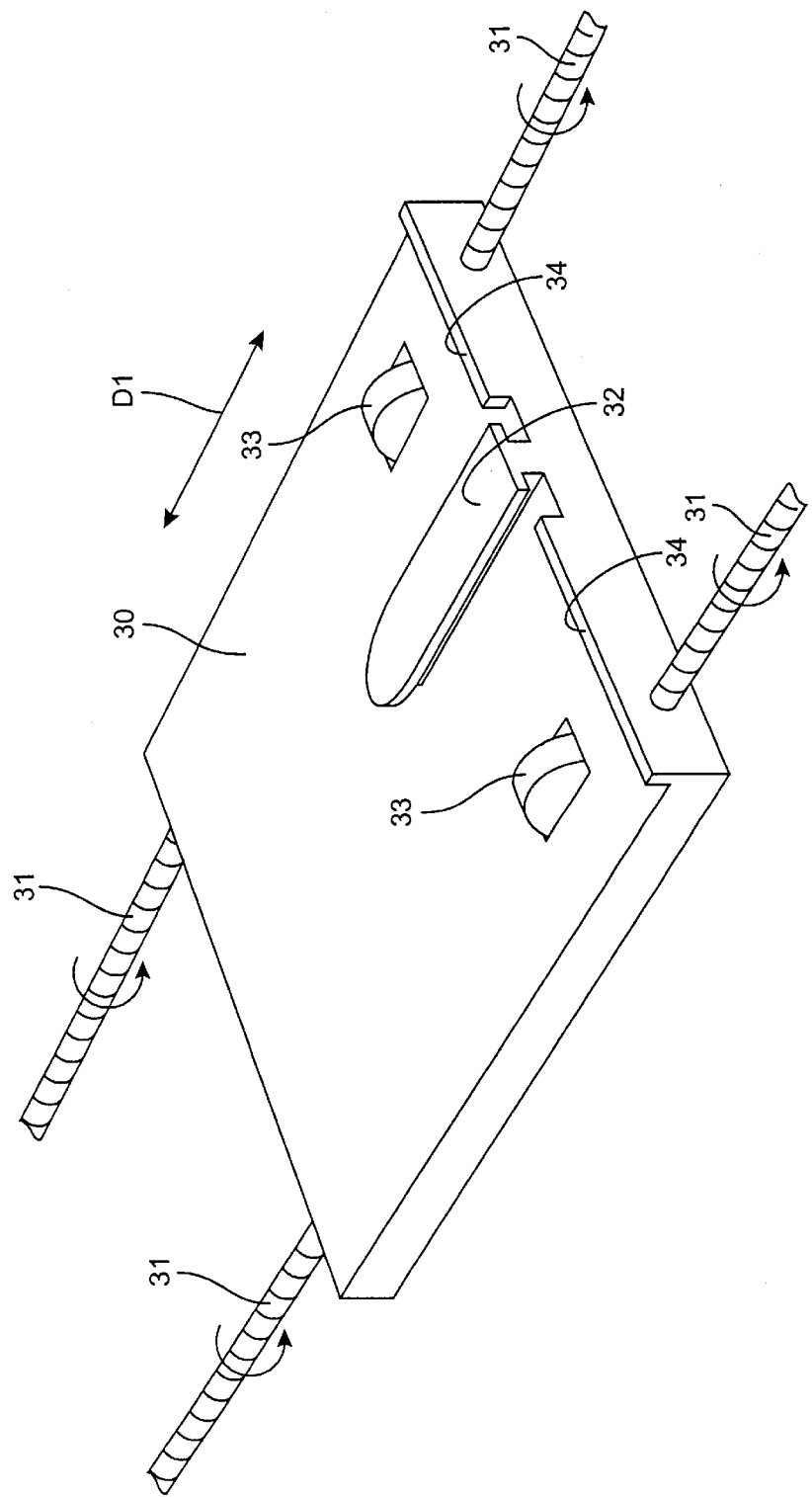
FIG. 9 is a perspective view of a shuttle for moving an imaging cassette within the housing of the device.

(c) Cassette Infeed Mechanism:

Further details of shuttle 30 are illustrated in FIG. 9. Preferably, shuttle 30 is constructed in a manner such that it securely latches or grabs onto cassette 20. In preferred aspects, shuttle 30 comprises one or more alignment guides which ensure that cassette 20 is centered thereon. In one preferred aspect, an elevated cleat 32 is provided. One or more detent rollers 33 may also be provided. The movement of shuttle 30 moves back and forth in direction D1 and is controlled by shuttle positioning assembly 31 (which may optionally comprise a worm gear).

Figure 10:
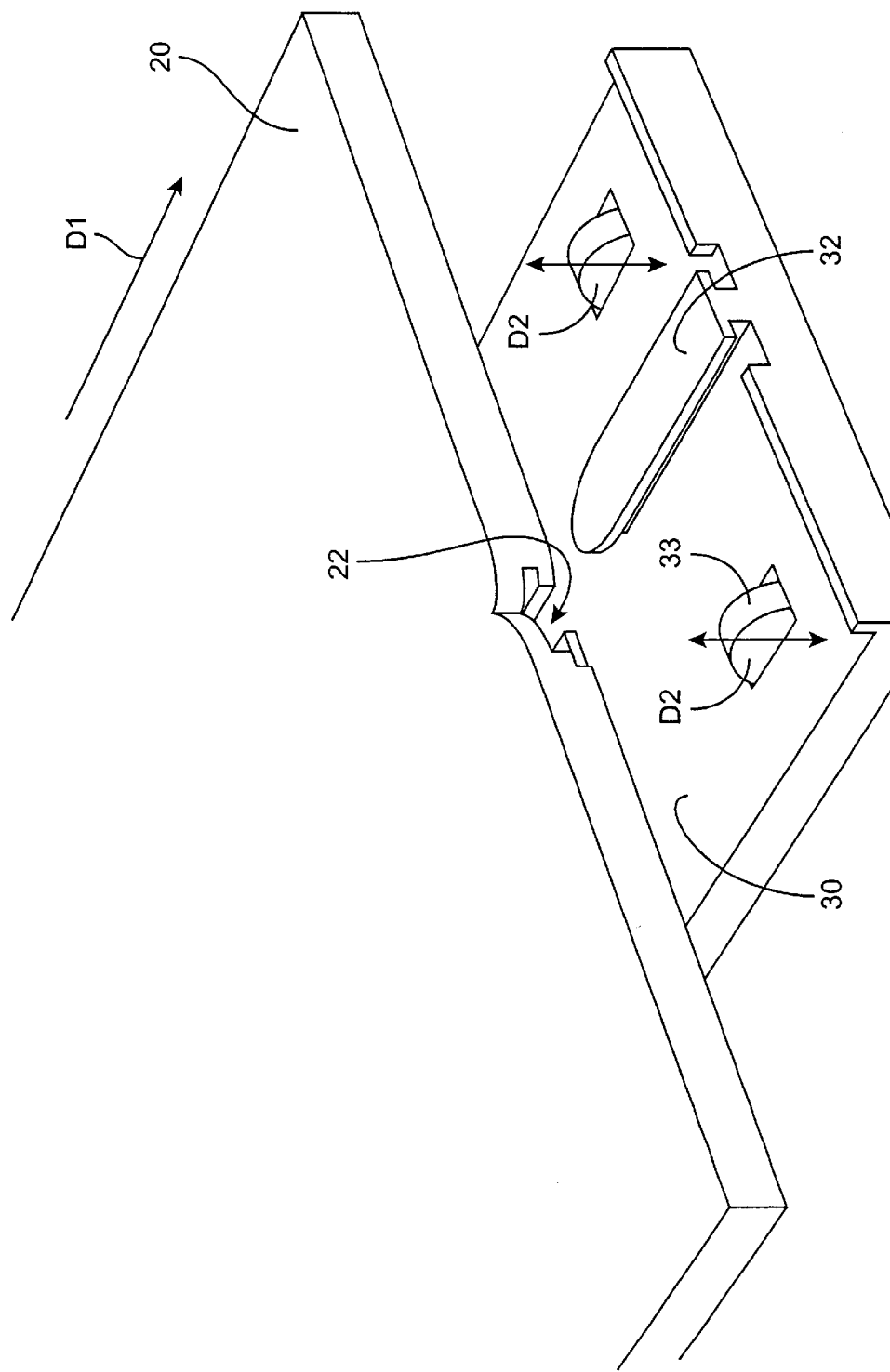
FIG. 10 is an illustration of an imaging plate cassette approaching the distal end of the shuttle.
Figure 11:
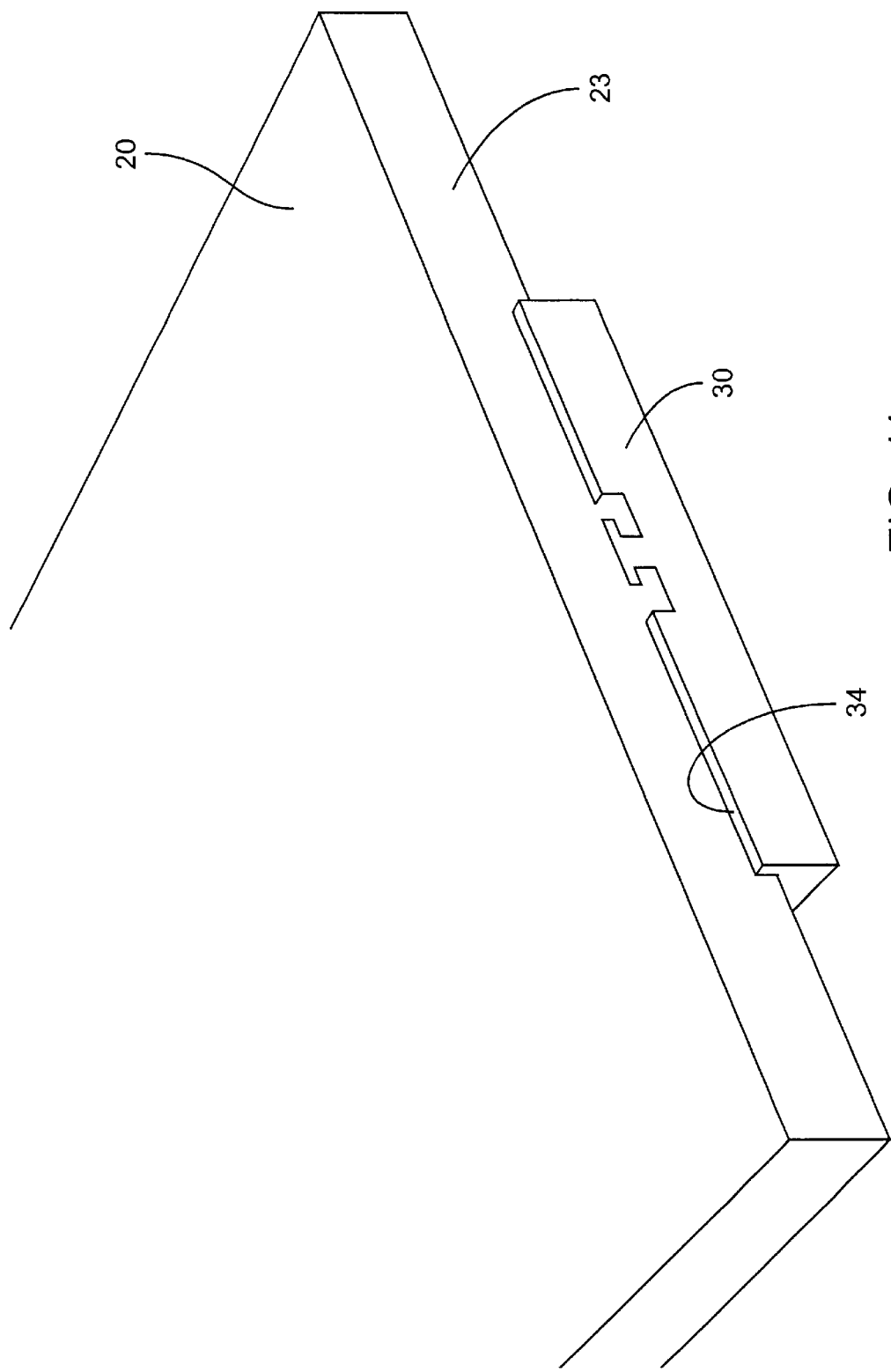
FIG. 11 is an illustration of the imaging plate cassette interlocked with the shuttle.

As shown in FIG. 10, cassette 20 is initially moved in direction D1 while shuttle 30 remains at a fixed position. (This occurs when the operator initially hand places cassette 20 through slot 12). (See FIG. 1) Cassette 20 preferably has a center slot 22 which mates with elevated cleat 32 such that cassette 20 is firmly centered on shuttle 30. In addition, cassette 20 may have a pair of recesses on is underside (not shown) which mate with depressible rollers 33. Specifically, each of depressible rollers 33 preferably are spring loaded to move up and down in direction D2 Accordingly, when cassette 20 is being slipped across the surface of shuttle 30, depressible rollers 33 are pushed down (by the underside of cassette 20) into the body of shuttle 30. When cassette 20 reaches the position shown in FIG. 11, optional backstops 34 projecting upwardly from the back end of shuttle will rest against the front end 23 of cassette 20. When cassette 20 reaches this final position, depressible rollers 33 will lock upward into the recesses (not shown) on the underside of cassette 20, holding cassette 20 in a secured (and centered) position on shuttle 30. In an optional preferred aspect, hooks deploy to lock the cassette in place on the shuttle when the cassette reaches its final (i.e.: fully received into housing 11) position.

In optional preferred aspects, different sized cassettes may advantageously be formed with their distal and bottom surfaces which engage the alignment/detent mechanisms at the same location, such that different sized cassettes 20 can be grasped by the same alignment/detent mechanisms on shuttle 30.

Figure 20:
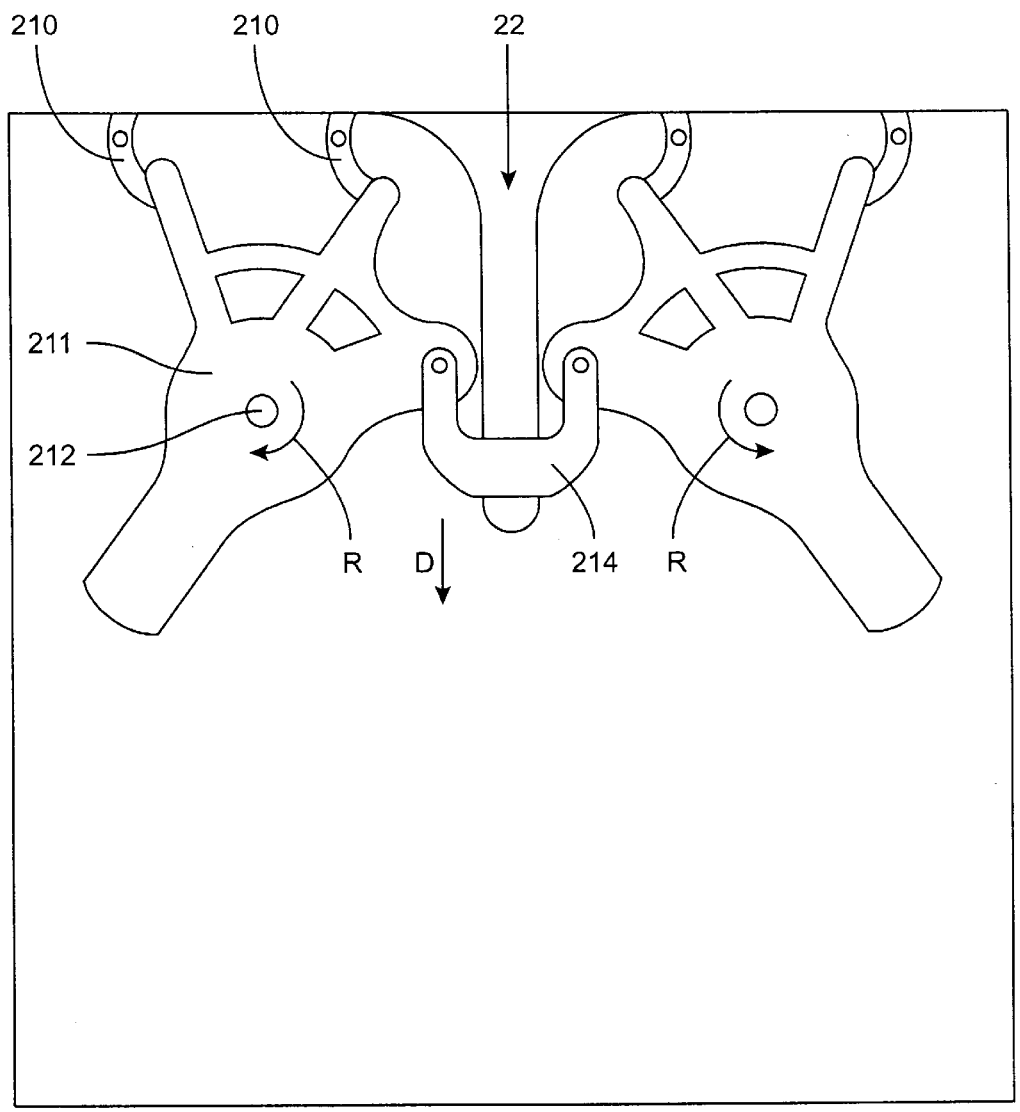
FIG. 20 is a schematic of the latching system of an exemplary imaging plate cassette.

In preferred aspects, cassette 20 may be made such that when elevated cleat 32 is received within center slot 22, it releases locking latches 210 (FIG. 20) which permits the cassette to be opened. In a preferred embodiment, the actuation mechanisms 211 for these latches are balanced about their pivot points 212 such that elevated cleat 32 pushes against slide mechanism 214, moving slide mechanism in direction D, thus causing actuation mechanisms 211 to rotate in direction R, unlatching latches 212, thereby unlocking cassette 20 (such that its top cover 21 can be opened. Advantageously, pivot points 212 are disposed at the center f gravity of actuation mechanisms 211 so that impacts to the cassette such as when dropped will not cause the latches to disengage.

Further details of an optional system for opening top cover 21 of cassette 20 are shown in the sequential operation of FIGS. 16 and 17. FIG. 16 illustrates a view of the cassette 20/shuttle 30 assembly at a position where it has been partially received into housing 11. A claw 100 is slidably movable along a pair of slots 101 (which are preferably positioned on either side of the cassette 20/shuttle 30 assembly, and thus shown in dotted lines). A spring 102 is connected to a fixed point 103 (preferably on housing 11). As shuttle 30 moves in direction D1 towards its final position (FIG. 17), claw 101 will latch onto top cover 21, pulling it upwardly thereby opening cassette top cover 21. In addition, spring 102 maintains a bias in a direction opposite to the direction in which cassette 20 is inserted, thereby maintaining a constant pressure on the contact between claw 1000 and top cover 21 such that claw 100 does not slip off top cover 21 as cassette 20 moves with shuttle 30. It is to be understood that the present invention also comprises a comparable system in which a bottom cover of cassette 20 is instead opened.

(d) Scanner/Imaging Plate Transportation Systems and Outfeed Area:

As illustrated in FIG. 5, imaging plate 40 is positioned to move across the surface of reference plate 71 of scanner assembly 70 by friction belt roller 60. Further preferred details of this aspect of the present invention are seen in FIGS. 12 to 15, as follows.

Figure 12:
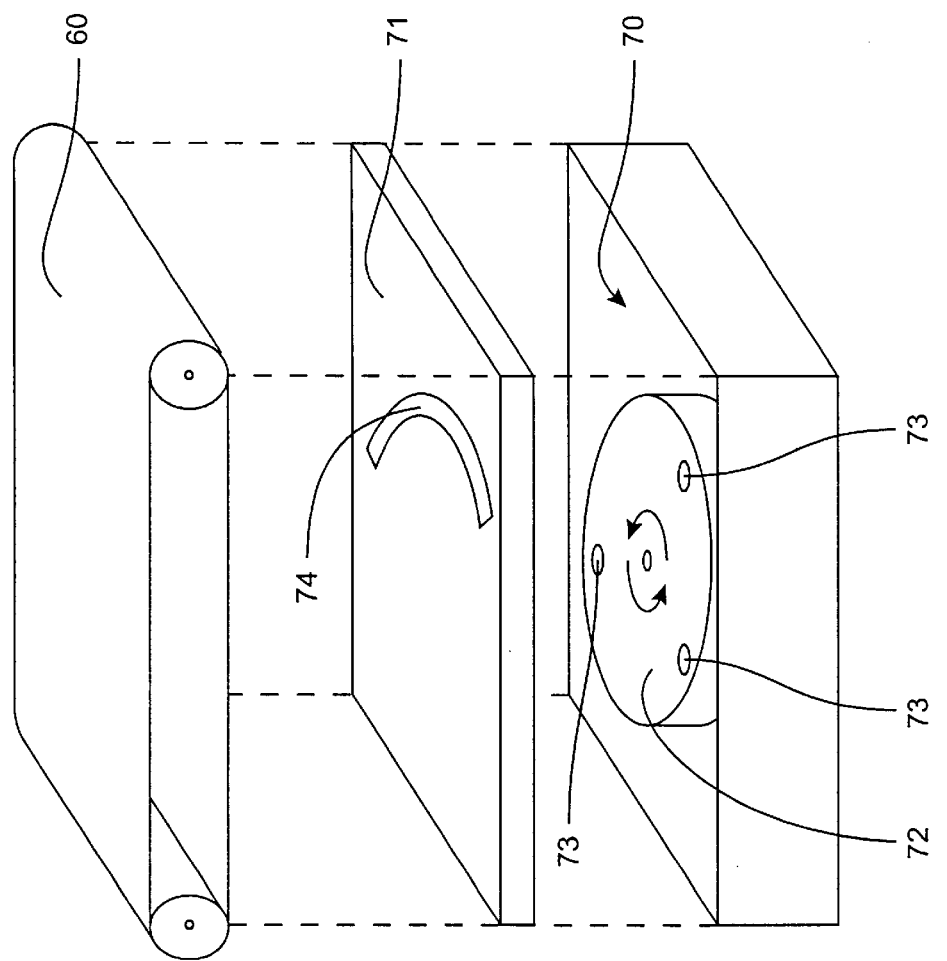
FIG. 12 is an exploded perspective view of the scanner with reference plate and friction roller belt thereover.

FIG. 12 is an exploded perspective view of the present system. Scanner assembly 70 preferably comprises a multi-head rotary scanner 72 having a plurality of scanning heads 73, although single-head scanners and scanners which scan in a back and forth in a straight scan path (as opposed to moving around a rotary scan path) may instead be used, all keeping within the scope of the present invention. Also, in a preferred aspect, the present rotary scanner has three scanning heads 73 (spaced 120° apart from one another), however, systems having other numbers of scanning heads are also contemplated in accordance with the present invention.

Figure 13:
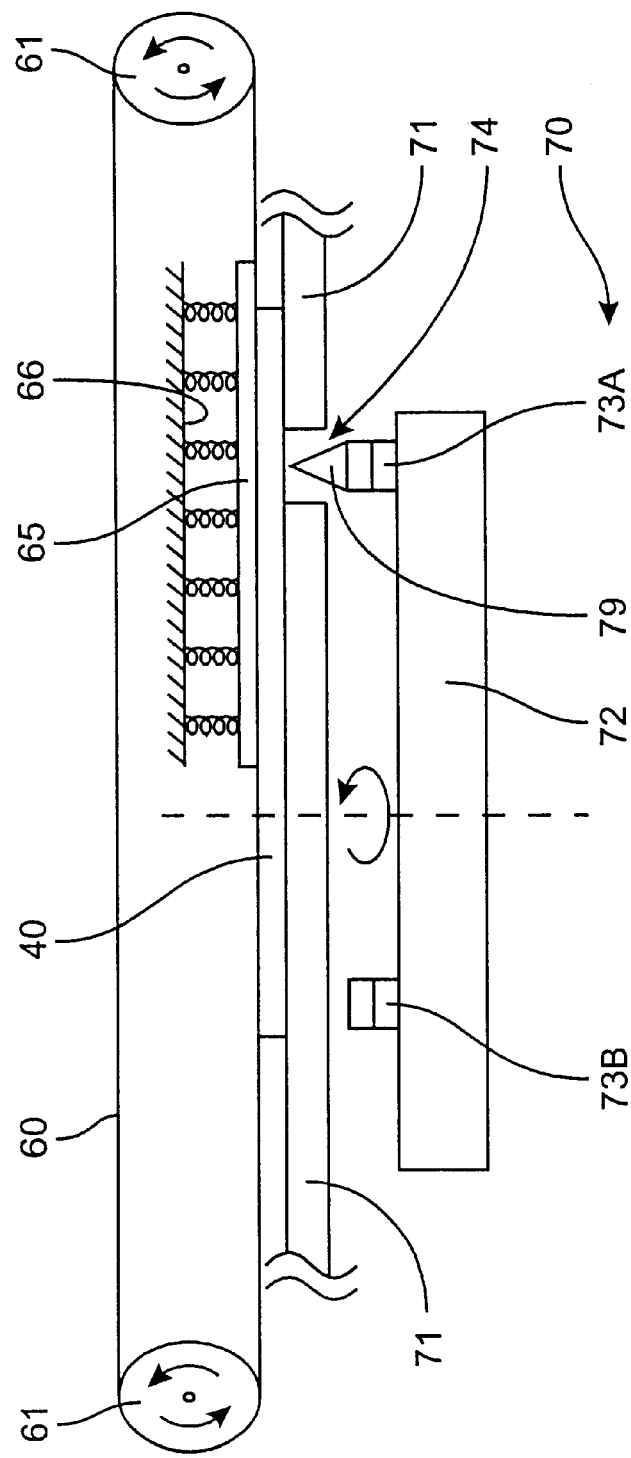
FIG. 13 is a side elevation sectional view of the imaging plate being scanned.
Figure 14:
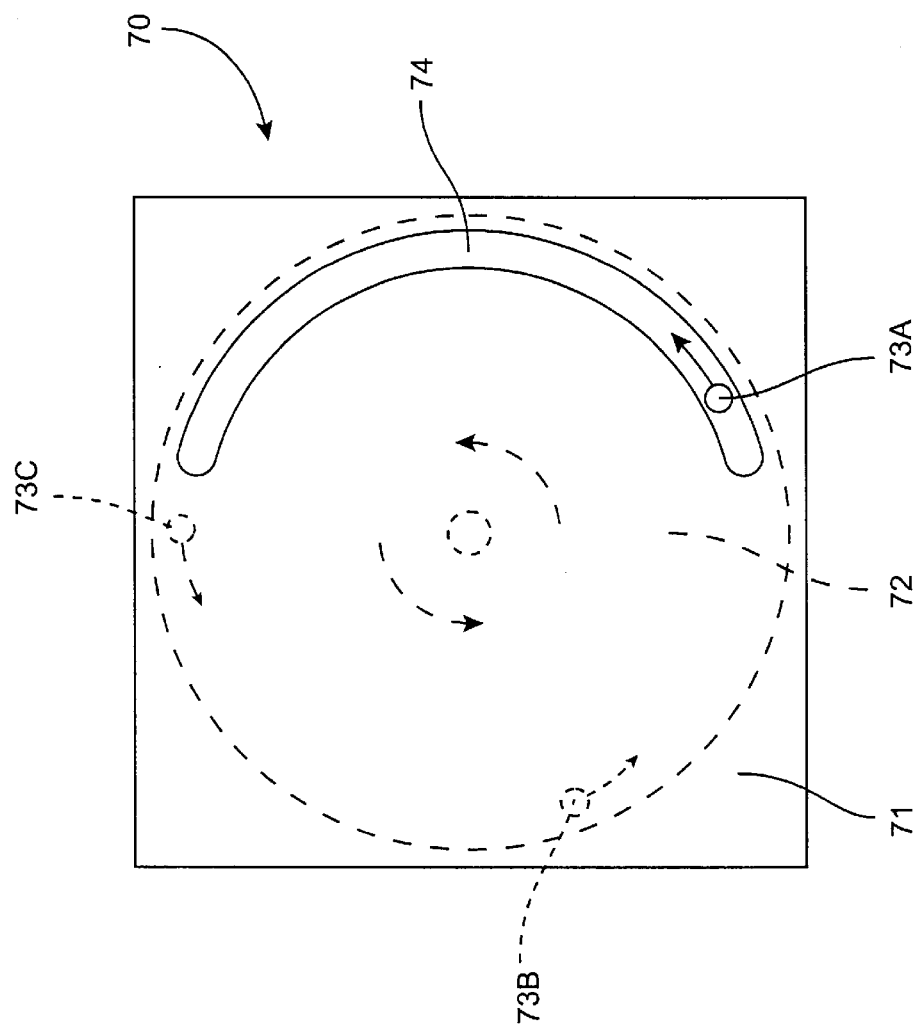
FIG. 14 is a top plan view of the scanner.

As can be seen in FIGS. 12 to 14, reference plate 71 preferably has a curved slot 74 passing therethrough. Curved slot 74 is positioned directly above the path of travel of successive scanning heads 73. Accordingly, as each successive scanning head 73 passes along slot 74, it scans in a curved line across the face of imaging plate 40. Slot 74 is preferably fabricated to be of a length such that only one of the three scanning heads 73 is passing thereunder at a time.

Preferably, reference plate 71 is made of a low friction material. Suitable examples include acrylic, glass or coated aluminum, although any suitable material is contemplated.

As can be seen in FIG. 13, a portion of friction belt roller 60 (which is wrapped around a pair of rollers 61 can be biased downwards against reference plate 71 by a pressure plate 65. In preferred aspects, pressure plate 65 comprises an element having a generally flat bottom surface which may be pushed (by springs, hydraulically, etc.) away from a fixed object or surface 66 such that pressure plate 65 holds imaging plate 40 tightly against reference plate 71 as rotation of rollers 61 causes imaging plate 61 to be passed (in either direction) over slot 74. Accordingly, a light-tight seal is maintained between scanner 70 and imaging plate 40 (preventing errant light from erasing assembly 50 from reaching the "scan area" (i.e. the location at slot 74 at which imaging plate 40 is actually scanned). A scanning laser beam 79 which is emitted from scanning head 73A is shown.

FIG. 14 shows a top plan view of reference plate 71 (having slot 74 along which scanning heads &3A, 73B and 73C pass in sequence as scanner 70 is rotated.

Figure 15:
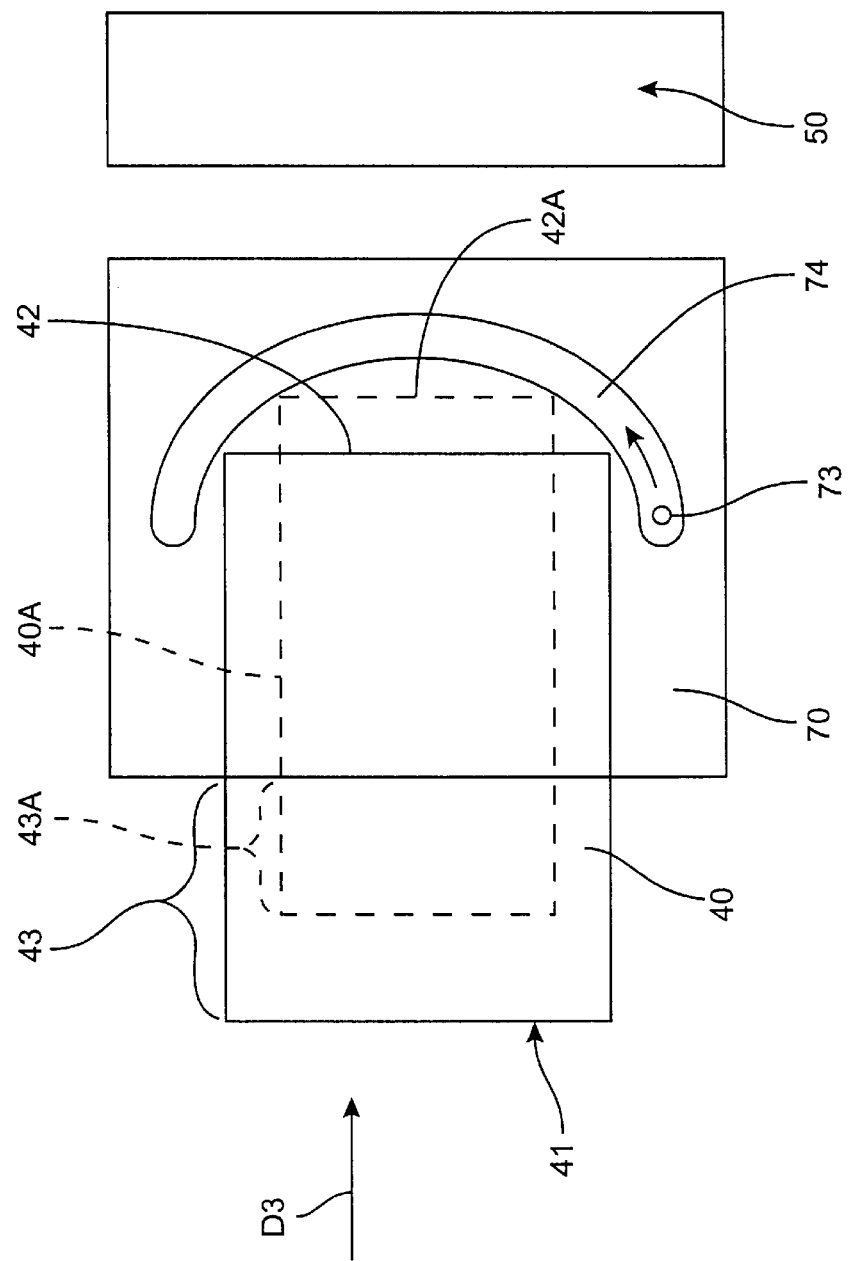
FIG. 15 is a top plan view of the scanner and erasing assembly showing the position of the imaging plate prior to the commencement of scanning.

FIG. 15 illustrates the position occupied by imaging plate 40 prior to the start of scanning. As explained above, successive scanning heads 73 move along positioned below curved groove 74 thereby scanning across the (bottom facing) surface of imaging plate 40. As can be appreciated, it is only necessary to initially move imaging plate 40 a distance such that its proximal end 42 is positioned distal to slot 74 prior to scanning.

Therefore, as can be seen, the width of any particular imaging plate will in part determine the position at which such imaging plate will be located prior to commencing scanning (At which time imaging plate 40 is moved in direction D3 across the scanner). Specifically, in cases when wider imaging plates are used, they must be positioned farther back (i.e. farther away from erasing assembly 50) on the face of the scanner. Conversely, when narrower imaging plates (such as plate 40A shown in dotted lies) are used, they may be positioned farther forward (i.e.: closer to erasing assembly 50) on the face of the scanner at the commencement of scanning. Thus, (a larger sized) portion 43 of (a larger sized) imaging plate 40 is received within outfeed area 80 (FIG. 5), whereas (a smaller sized) portion 43A of (a smaller sized) imaging plate 40A is received in outfeed area 80.

Accordingly, the full length of outfeed area 80 which is occupied by a portion of imaging plate 40 prior to commencement of scanning depends upon the size of image plate 40 which is scanned and erased by the present system. Regardless of the size of imaging plate 40 which is used, however, an advantage of the present system is that curved outfeed area 80 need not exceed the length of the imaging plate (since a portion of the imaging plate can remain positioned on top of reference plate 71 as long as its proximal end 42 is positioned behind slot 74.

Figure 19:
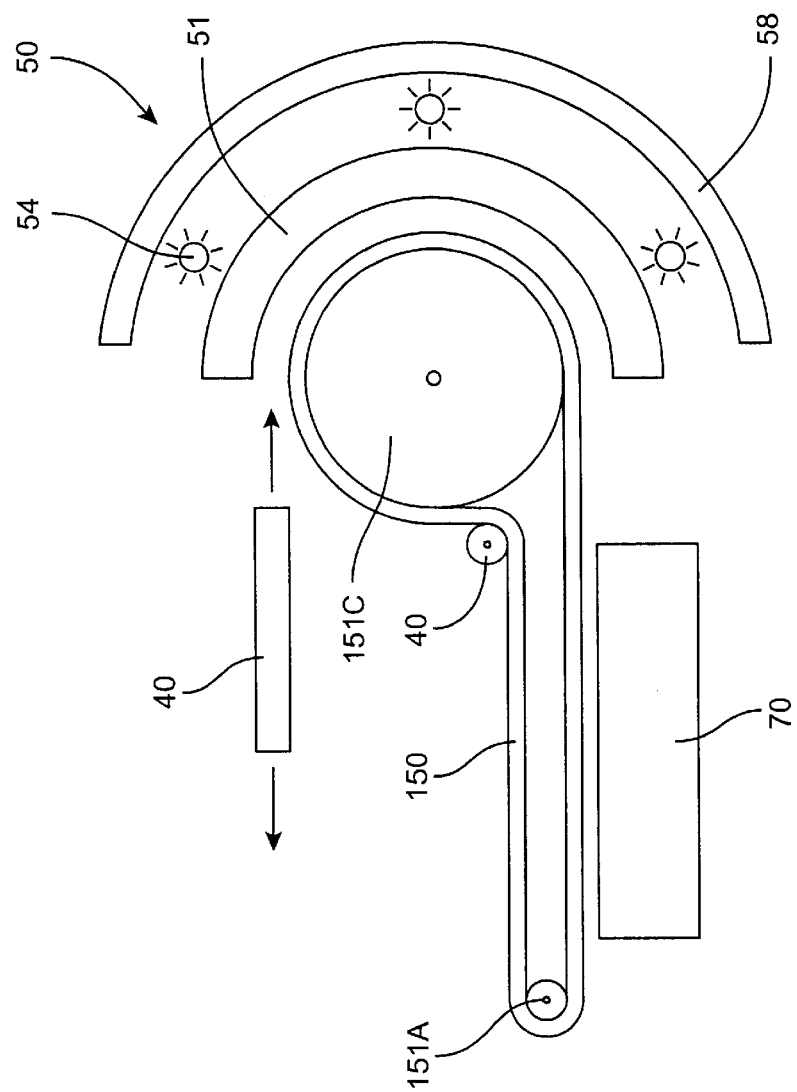
FIG. 19 is a side schematic view of a system comprising a single continuous belt for moving an imaging plate back and forth through an erasing assembly and past a scanner.

Alternatively, as shown in FIG. 19, a continuous friction belt 150 can be wrapped around a plurality of rollers 151A, 151B and 151C such that this same belt 150 can be used to both pass imaging plate 40 through curved erasing assembly 50 and past scanner 70.

Figure 18:
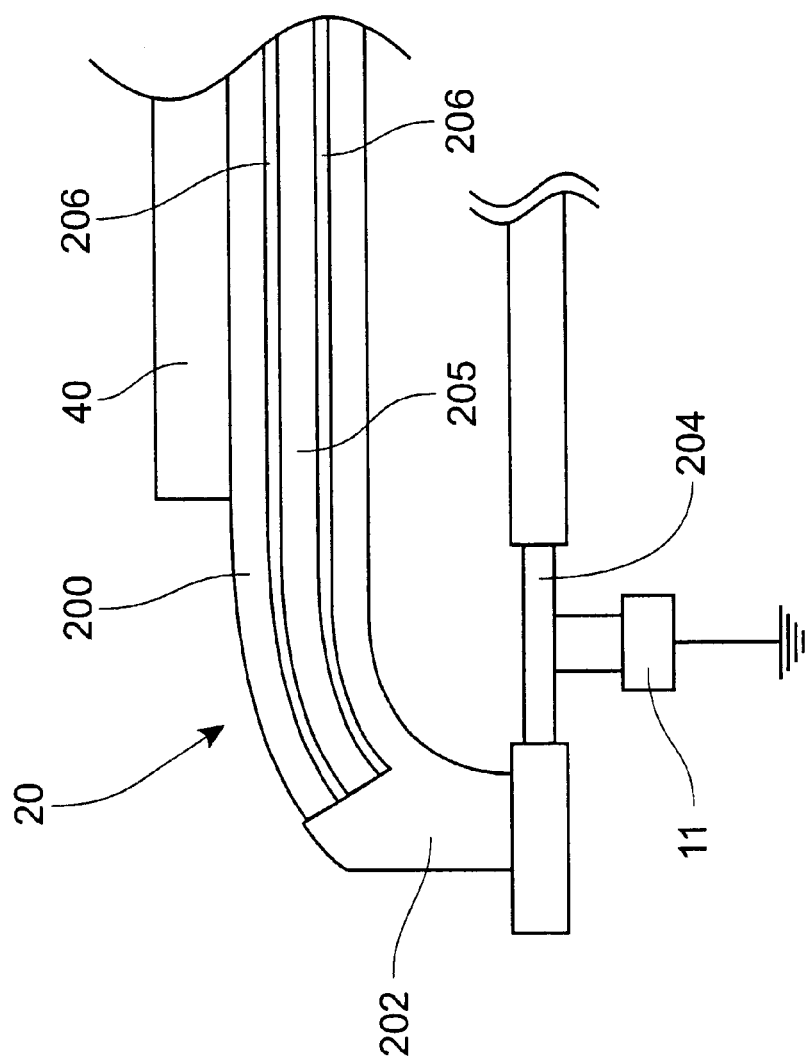
FIG. 18 is a side sectional elevation view of an edge of a preferred imaging plate cassette (with an imaging plate resting therein).

(e) Antistatic Cassette Considerations:

Lastly, FIG. 18 shows a sectional close-up end view of an anti-static system which can be incorporated in cassette 20. Specifically, as imaging plate 40 is repeatedly removed from, and inserted back into, cassette 20, static may tend to build up.

In accordance with the present invention, a fabric liner 200 may be positioned in contact with a conductive plastic 202 which is grounded to an exterior contact on the cassette (for example, electronic circuit 204). Cassette electronic circuit 204 is then preferably grounded to housing 11 such that built up static energy is dissipated each time any particular cassette 20 is positioned within housing 11. A standard lead layer 205 is preferably positioned under fabric liner 200 with tape layers 206 holding the assembly together.

In an alternate preferred embodiment, an interior conductive fabric liner 200 is electrically connected to an exterior contact on the cassette where it can contact a grounded point on the housing 11 of system 10.

What is claimed is:

1. A combined imaging plate scanning and erasing system, comprising:
   (a) a housing;
   (b) an imaging plate cassette infeed assembly positioned within the housing, the imaging plate cassette infeed assembly comprising:
      (i) a mechanism to pull an imaging plate cassette into the housing;
      (ii) a mechanism to open the imaging plate cassette; and
      (iii) a mechanism to remove an imaging plate from the cassette;
   (c) a scanner positioned within the housing;
   (d) a curved path erasing assembly positioned between the imaging plate infeed assembly and the scanner; and
   (e) an imaging plate transportation assembly to move the imaging plate back and forth in a path extending from the imaging plate cassette, past the erasing assembly and through a scan area adjacent to the scanner.

2. The system of claim 1, wherein,
the imaging plate cassette infeed assembly is positioned within an upper portion of the housing; and
the scanner is positioned within a lower portion of the housing.

3. The system of claim 1, wherein,
the imaging plate cassette infeed assembly is positioned within a lower portion of the housing; and
the scanner is positioned within an upper portion of the housing.

4. The system of claim 1, wherein,
the imaging plate cassette infeed assembly is positioned side by side the scanner.

5. The system of claim 1, wherein,
the imaging plate cassette infeed assembly positions the imaging cassette such that the imaging plate cassette and the scanner are positioned one on top of another when the cassette is opened.

6. The system of claim 1, wherein,
the imaging plate cassette infeed assembly moves the imaging cassette back and forth in a path which is parallel to the direction that the imaging plate moves when the imaging plate is scanned by the scanner.

7. The system of claim 1, wherein an imaging plate is flipped over as it moves along the path extending from the imaging plate cassette, through the curved path erasing assembly and into a scan area where the imaging plate can be scanned by the scanner.

8. The system of claim 1, wherein the scanner and erasing assembly are positioned sufficiently close together such that portions of the imaging plate can be erased while other portions of the imaging plate are being scanned.

9. The system of claim 1, wherein the mechanism to pull an imaging plate cassette into the housing comprises:
   a shuttle which holds onto the imaging plate cassette; and
   a shuttle positioning assembly which moves the shuttle back and forth within the housing.

10. The system of claim 9, wherein the shuttle positioning assembly moves the shuttle a distance sufficient such that the entire cassette can be pulled into the housing.

11. The system of claim 9, wherein the shuttle comprises:
    an alignment guide to center the imaging plate cassette thereon.

12. The system of claim 11, wherein the alignment guide comprises an elevated cleat.

13. The system of claim 12, further comprising:
    the imaging plate cassette, wherein the imaging plate cassette has a slot dimensioned to mate with the elevated cleat.

14. The system of claim 13, wherein the elevated cleat unlatches a latch in the slot on the cassette, thereby unlocking the cassette, permitting the cassette to be opened.

15. The system of claim 9, wherein the shuttle comprises:
    at least one detent mechanism to securely hold the cassette thereon.

16. The system of claim 15, wherein the at least one detent mechanism comprises:
    a pair of depressible spring rollers.

17. The system of claim 15, further comprising:
    the imaging plate cassette, wherein the imaging plate cassette has at least one recess thereon which is dimensioned to mate with the detent mechanism.

18. The system of claim 9, wherein the shuttle comprises a structure which prevents motion of the cassette beyond a reference position when the cassette is slidably positioned onto the shuttle.

19. The system of claim 18, wherein the structure comprises a backstop.

20. The system of claim 9, wherein the mechanism to open the imaging plate cassette comprises:
    a claw dimensioned to latch onto a cover of the cassette, and pull the cover open as the shuttle moves the cassette to a final position within the housing.

21. The system of claim 20, wherein the claw is biased such that it maintains a constant grip on the cover of the cassette while opening the cassette.

22. The system of claim 20, wherein the claw moves along a track while opening the cassette.

23. The system of claim 20, wherein the cover is a top cover of the cassette.

24. The system of claim 20, wherein the cover is a bottom cover of the cassette.

25. The system of claim 1, wherein the mechanism to pull the imaging plate out of the cassette comprises:
    a friction grab roller which is positionable against the imaging plate.

26. The system of claim 1, wherein the curved path erasing assembly comprises:
- a curved window; and
- at least one erasing light source positioned adjacent to the curved window so as to direct erasing light through the curved window.

27. The system of claim 26, further comprising:
- a highly reflective surface disposed around the at least one erasing light source, such that the at least one erasing light source is positioned between the curved window and the highly reflective surface.

28. The system of claim 26, further comprising:
- a highly reflective backing surface disposed on the side of the window opposite the at least one erasing light source, such that when the imaging plate occupies a portion of the area exposed by the window, the remainder of the area exposed by the window exposes some portion of the highly reflective backing surface.

29. The system of claim 26, wherein the at least one light source comprises a plurality of LEDs.

30. The system of claim 29, wherein the LEDs are white LEDs.

31. The system of claim 29, wherein the plurality of LEDs comprise a plurality of LED arrays which are spaced apart around the curved window.

32. The system of claim 31, wherein each of the LED arrays comprise a narrow elongated array disposed perpendicular to the path extending from the imaging plate cassette, past the erasing assembly and across the scanner.

33. The system of claim 29, wherein the plurality of LEDs are mounted on a flexible circuit board conforming to the shape of the curved path erasing assembly.

34. The system of claim 30, wherein areas of the curved window disposed between at least some of the LED's are covered by a highly reflective material.

35. The system of claim 34, wherein the highly reflective material is selected from the group consisting of a mirror, white paint, white silkscreen, white plastic and aluminized plastic.

36. The system of claim 27, wherein the at least one light source comprises at least one fluorescent tube.

37. The system of claim 36, wherein the at least one fluorescent tube comprises either a hot or cold cathode fluorescent tube.

38. The system of claim 36, wherein the at least one fluorescent tube comprises a plurality of fluorescent tubes which are spaced apart around the circumference of the curved window.

39. The system of claim 36, wherein the at least one fluorescent tube comprises a plurality of fluorescent tubes which are spaced apart along the length of the curved window.

40. The system of claim 36, wherein the highly reflective surface comprises a surface covered by a highly reflective material selected from the group consisting of a mirror, white paint, white silkscreen, white plastic and aluminized plastic.

41. The system of claim 36, further comprising:
- at least one heating element positioned adjacent the at least one fluorescent tube.

42. The system of claim 36, further comprising:
- a thermal blanket positioned adjacent the at least one fluorescent tube.

43. The system of claim 26, wherein the curved window is made of a low friction material.

44. The system of claim 43, wherein the low friction material is selected from the group consisting of acrylic, polycarbonate, or glass.

45. The system of claim 26, further comprising:
- a curved member positioned spaced apart from the curved window at a distance sufficient for an imaging plate to pass therebetween.

46. The system of claim 45, wherein the curved member is made of a low friction material.

47. The system of claim 46, wherein the low friction material is selected from the group consisting of acrylic, polycarbonate, glass, zinc coated steel and electroless nickel with Teflon impregnation.

48. The system of claim 45, wherein the curved window wraps around the curved member.

49. The system of claim 45, wherein the curved member wraps around the curved window.

50. The system of claim 45, wherein the curved member and the curved window can be moved apart thereby facilitating the clearing of a jam.

51. The system of claim 50, wherein the curved member and the curved window are attached to separate components of the system.

52. The system of claim 26, wherein the at least one erasing light source comprises a light source selected from the group consisting of a gas discharge lamp, a Na lamp, an Ne lamp, a metal halide lamp and an Xe lamp.

53. The system of claim 26, wherein the at least one erasing light source comprises a white light source.

54. The system of claim 1, wherein the curved path erasing assembly comprises:
- a light transmissive drum;
- at least one erasing light source positioned within the drum; and
- a curved member spaced apart from the drum, the curved member wrapping at least partially around the drum.

55. The system of claim 54, wherein the light transmissive drum is a rotating drum.

56. The system of claim 1, wherein the scanner comprises:
- a multi-head rotating scanner.

57. The system of claim 56, wherein the multi-head rotating scanner has three scanning heads.

58. The system of claims 1 or 56, wherein the scanner comprises a movable scanning head, further comprising:
- a reference plate covering the scanner, the reference plate having a slot passing therethrough wherein light from the movable scanning head passes through the slot thereby reading an image stored in the imaging plate as the imaging plate moved across the reference plate.

59. The system of claim 58, wherein the reference plate is made of a low friction material.

60. The system of claim 59, wherein the low friction material is selected from the group consisting of acrylic, glass or coated aluminum.

61. The system of claim 58, wherein the imaging plate transportation assembly comprises:
- a friction belt roller assembly for sliding the imaging plate across the surface of the reference plate.

62. The system of claim 61, further comprising:
- a pressure plate which biases the friction belt against the surface of the reference plate.

63. The system of claim 62, wherein the friction belt roller assembly comprises:
- a pair of rollers; and
- a friction belt wrapped therearound.

64. The system of claim 63, wherein the pressure plate biases a portion of the friction belt which is disposed between the pair of rollers.

65. The system of claim 1, wherein the imaging plate transportation system comprises:
a plurality of friction grab rollers positioned to move the imaging plate past the erasing assembly.

66. The system of claim 65, further comprising:
a friction belt roller assembly for moving the imaging plate through the scan area.

67. The system of claim 65, wherein the friction belt roller assembly is positioned to move the imaging plate across a reference plate covering the scanner.

68. The system of claim 1, wherein the imaging plate transportation system comprises:
a continuous friction belt wrapped around a plurality of rollers to move the imaging plate past the erasing assembly and through the scan area.

69. The system of claim 1, further comprising:
an imaging plate outfeed area positioned distal to the scanner.

70. The system of claim 69, wherein the outfeed area is curved.

71. The system of claim 69, wherein the path extending from the imaging plate cassette, past the erasing assembly and through a scan area adjacent to the scanner also extends into the outfeed area.

72. The system of claim 69, wherein the length of the outfeed area is less than the length of the scanner.

73. The system of claim 1, further comprising:
the imaging plate cassette.

74. The system of claim 73, wherein the imaging plate cassette comprises:
an interior conductive fabric layer covering a grounded conductive plastic member.

75. The system of claim 73, wherein
wherein the conductive plastic member is grounded to an exterior contact on the housing of the combined imaging plate scanning and erasing system.

76. The system of claim 73, wherein the imaging plate cassette further comprises an electronic circuit, and wherein the conductive plastic member is grounded to the electronic circuit and the electronic circuit is grounded to the housing of the combined imaging plate scanning and erasing system.

77. The system of claim 73, wherein the imaging plate cassette further comprises:
a latching mechanism with balanced actuator members thereby reducing the tendency for the latching mechanism to unlatch upon sudden shocks.

78. A method of scanning and then erasing an imaging plate with a combined imaging plate scanning and erasing system, comprising:
(a) inserting an imaging plate cassette into the combined imaging plate scanning and erasing system, wherein the imaging plate is stored within the imaging plate cassette;
(b) pulling the imaging plate cassette into the combined imaging plate scanning and erasing system;
(c) opening the imaging plate cassette;
(d) removing the imaging plate from the imaging plate cassette;
(e) moving the imaging plate in a path extending past a curved erasing assembly and then through a scan area adjacent to a scanner;
(f) scanning an image on the imaging plate with the scanner;
(g) moving the imaging plate back through the scan area and then back past the erasing assembly;
(h) erasing the imaging plate with the erasing assembly;
(i) placing the imaging plate back into the imaging plate cassette;
(j) closing the imaging plate cassette; and
(k) pushing the imaging plate cassette out of the combined imaging plate scanning and erasing system.

79. The method of claim 78, further comprising:
moving at least a distal portion of the imaging plate into an outfeed area positioned distal to the scanner prior to scanning an image on the imaging plate.

80. The method of claim 79, wherein the imaging plate reverses direction after it has been moved into the outfeed area positioned distal to the scanner.

81. The method of claim 78, further comprising:
moving at least a portion of the imaging plate into an outfeed area positioned distal to the scanner after scanning an image on the imaging plate.

82. The method of claim 81, wherein the imaging plate reverses direction after it has been moved into the outfeed area positioned distal to the scanner.

83. The method of claim 78, wherein pulling the imaging plate cassette into the combined imaging plate scanning and erasing system comprises:
holding onto the imaging plate cassette with a movable shuttle; and
moving the shuttle so as to pull the cassette into the combined imaging plate scanning and erasing system.

84. The method of claim 83, wherein the shuttle is moved a distance sufficient to pull the entire cassette into the combined imaging plate scanning and erasing system.

85. The method of claim 83, wherein the imaging cassette such that the imaging plate cassette and the scanner are positioned one on top of another when the cassette is opened.

86. The method of claim 83, wherein holding onto the imaging plate cassette with the movable shuttle comprises:
mating an alignment guide on the movable shuttle with a slot on the imaging plate cassette.

87. The method of claim 78, wherein the imaging plate cassette is opened by moving the shuttle a distance sufficient such that a movable claw grabs onto a cover of the cassette and pulls the cover open as the shuttle moves the cassette to a final position within the housing.

88. The method of claim 78, wherein the imaging plate is removed from the imaging plate cassette by
pulling the imaging plate out of the imaging plate cassette with a friction grab roller.

89. The method of claim 78, wherein erasing the image on the imaging plate comprises:
passing the imaging plate along a curved window, wherein at least one erasing light source is positioned to direct erasing light through the curved window and onto the imaging plate.

90. The method of claim 89, wherein the at least one light source comprises a plurality of LEDs.

91. The method of claim 89, wherein the at least one light source comprises at least one fluorescent tube.

92. The method of claim 91, wherein the at least one light source further comprises a plurality of parallel fluorescent tubes spaced apart by at least 1.2 times the diameter of the fluorescent tubes thereby allowing light from the back side of the fluorescent tubes to reach the imaging plate.

93. The method of claim 78, wherein light from the at least one fluorescent tube is reflected through the curved window by a highly reflective surface disposed around the at least one fluorescent tube positioned opposite to the curved window.

94. The method of claim 89, wherein passing the imaging plate along a curved window comprises:
  sliding the imaging plate along the surface of the curved window.

95. The method of claim 89, wherein passing the imaging plate along a curved window comprises:
  passing the imaging plate between the curved window and a curved member spaced apart from the curved window.

96. The method of claim 90, wherein areas of the curved window disposed between at least some of the LED's are covered by a highly reflective material.

97. The method of claim 78, wherein scanning an image on the imaging plate with the scanner comprises:
  passing the imaging plate through the scan area disposed adjacent to the scanner.

98. The method of claim 97, wherein the scanner comprises a reference plate having a slot passing therethrough and wherein light from a movable scanning head in the scanner passes through the slot, further comprising:
  moving the scanning head to scan an image stored in the imaging plate; while sliding the imaging plate across the reference plate.

99. The method of claim 97, wherein moving the scanning head to scan an image stored in the imaging plate comprises:
  rotating a multi-head scanner such that sequential scanning heads pass along the slot in the reference plate.

100. The method of claim 97, wherein a friction belt roller slides the imaging plate across the reference plate.

101. The method of claim 78, wherein a portion of the imaging plate is erased at the same time that another portion of the imaging plate is being scanned.

102. The method of claim 100, wherein the friction belt presses the imaging plate against the reference plate thereby preventing eraser light from reaching unread portions of the imaging plate.

103. The method of claim 89, wherein the eraser light is off while the imaging plate passes past it prior to scanning and then is turned on thereafter thereby erasing portions of the imaging plate only after they have been scanned.

104. A method of erasing an imaging plate with a combined imaging plate scanning and erasing system, comprising:
  (a) inserting an imaging plate cassette into the combined imaging plate scanning and erasing system, wherein the imaging plate is stored within the imaging plate cassette;
  (b) pulling the imaging plate cassette into the combined imaging plate scanning and erasing system;
  (c) opening the imaging plate cassette;
  (d) removing the imaging plate from the imaging plate cassette;
  (e) moving the imaging plate in a path extending past a curved erasing assembly and then through a scan area adjacent to a scanner;
  (f) moving the imaging plate back through the scan area and then back past the erasing assembly;
  (g) erasing the imaging plate with the erasing assembly both when performing each of (e) and (f);
  (h) placing the imaging plate back into the imaging plate cassette;
  (i) closing the imaging plate cassette; and
  (j) pushing the imaging plate cassette out of the combined imaging plate scanning and erasing system.

* * * * *